(12) United States Patent
Weitz et al.

(10) Patent No.: US 9,757,698 B2
(45) Date of Patent: Sep. 12, 2017

(54) FLUID INJECTION

(75) Inventors: David A. Weitz, Bolton, MA (US); Adam R. Abate, San Francisco, CA (US); Tony Hung, Peachtree City, GA (US); Pascaline Mary, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 957 days.

(21) Appl. No.: 13/379,782

(22) PCT Filed: Jun. 25, 2010

(86) PCT No.: PCT/US2010/040006
§ 371 (c)(1),
(2), (4) Date: Feb. 15, 2012

(87) PCT Pub. No.: WO2010/151776
PCT Pub. Date: Dec. 29, 2010

(65) Prior Publication Data
US 2012/0132288 A1    May 31, 2012

Related U.S. Application Data

(60) Provisional application No. 61/220,847, filed on Jun. 26, 2009.

(51) Int. Cl.
*F16K 99/00*     (2006.01)
*B01F 5/04*      (2006.01)
(Continued)

(52) U.S. Cl.
CPC ........ *B01F 5/0471* (2013.01); *B01F 13/0071* (2013.01); *B01F 13/0076* (2013.01);
(Continued)

(58) Field of Classification Search
CPC ........ B01L 2300/0867; B01L 3/50273; B01L 3/502784; B01L 2400/0415;
(Continued)

(56) References Cited

U.S. PATENT DOCUMENTS

| 4,279,345 A | 7/1981 | Allred |
| 5,512,131 A | 4/1996 | Kumar et al. |

(Continued)

FOREIGN PATENT DOCUMENTS

| EP | 0 718 038 B1 | 10/2002 |
| EP | 1533605 A2   | 5/2005  |

(Continued)

OTHER PUBLICATIONS

Australian Examination Report for Application No. AU 2010266010 dated Mar. 31, 2014.
(Continued)

*Primary Examiner* — Craig Schneider
*Assistant Examiner* — Josephine Trinidad-Borges
(74) *Attorney, Agent, or Firm* — Wolf, Greenfield & Sacks, P.C.

(57) ABSTRACT

The present invention generally relates to systems and methods for the control of fluids and, in some cases, to systems and methods for flowing a fluid into and/or out of other fluids. As examples, fluid may be injected into a droplet contained within a fluidic channel, or a fluid may be injected into a fluidic channel to create a droplet. In some embodiments, electrodes may be used to apply an electric field to one or more fluidic channels, e.g., proximate an intersection of at least two fluidic channels. For instance, a first fluid may be urged into and/or out of a second fluid, facilitated by the electric field. The electric field, in some cases, may disrupt an interface between a first fluid and at least one other fluid. Properties such as the volume, flow
(Continued)

rate, etc. of a first fluid being urged into and/or out of a second fluid can be controlled by controlling various properties of the fluid and/or a fluidic droplet, for example curvature of the fluidic droplet, and/or controlling the applied electric field.

18 Claims, 9 Drawing Sheets

(51) Int. Cl.
    *B01F 13/00*     (2006.01)
    *B01J 19/00*     (2006.01)
    *B01L 3/00*     (2006.01)
    *G01N 27/447*     (2006.01)
    *G01N 35/10*     (2006.01)

(52) U.S. Cl.
    CPC ..... *B01J 19/0093* (2013.01); *B01L 3/502784* (2013.01); *F16K 99/0051* (2013.01); *B01J 2219/00837* (2013.01); *B01J 2219/00853* (2013.01); *B01J 2219/00862* (2013.01); *B01J 2219/00889* (2013.01); *B01L 3/50273* (2013.01); *B01L 2300/0867* (2013.01); *B01L 2400/0415* (2013.01); *F16K 99/0042* (2013.01); *G01N 27/44791* (2013.01); *G01N 2035/1034* (2013.01); *Y10T 137/0391* (2015.04); *Y10T 137/206* (2015.04)

(58) Field of Classification Search
    CPC .......... B01J 2219/00889; B01J 19/0093; B01J 2219/00853; B01J 2219/00837; B01J 2219/00862; F16K 99/0051; F16K 99/0042; G01N 27/44791; G01N 2035/1034; B01F 5/0471; B01F 13/0076; B01F 13/0071; Y10T 137/0391; Y10T 137/206
    USPC .......... 137/3, 13, 827, 896, 897; 436/8, 178; 204/600, 601, 604; 422/504
    See application file for complete search history.

(56) References Cited

U.S. PATENT DOCUMENTS

| | | | |
|---|---|---|---|
| 6,149,789 A | 11/2000 | Benecke et al. | |
| 6,355,198 B1 | 3/2002 | Kim et al. | |
| 6,432,630 B1 | 8/2002 | Blankenstein | |
| 6,524,456 B1 | 2/2003 | Ramsey et al. | |
| 2001/0004964 A1* | 6/2001 | Manz .................. | C07K 1/26 204/453 |
| 2003/0015425 A1 | 1/2003 | Bohm et al. | |
| 2003/0226604 A1* | 12/2003 | Schlautmann et al. ....... | 137/827 |
| 2004/0007463 A1 | 1/2004 | Ramsey et al. | |
| 2004/0144939 A1* | 7/2004 | Giousouf et al. ........ | 251/129.01 |
| 2006/0163385 A1 | 7/2006 | Link et al. | |
| 2007/0003442 A1 | 1/2007 | Link et al. | |
| 2007/0195127 A1 | 8/2007 | Ahn et al. | |
| 2007/0227890 A1* | 10/2007 | Ramsey et al. ............... | 204/451 |
| 2008/0264797 A1 | 10/2008 | Pamula et al. | |
| 2014/0305799 A1 | 10/2014 | Link et al. | |

FOREIGN PATENT DOCUMENTS

| | | | | |
|---|---|---|---|---|
| GB | 2 097 692 A | | 11/1982 | |
| GB | 2453534 A | * | 4/2009 | ............. B01F 13/00 |
| IE | 20070072 A1 | | 9/2007 | |
| JP | 2003-507162 A | | 2/2003 | |
| JP | 2005-270894 A | | 10/2005 | |
| JP | 2006-523142 A | | 10/2006 | |
| WO | WO 96/29629 A2 | | 9/1996 | |
| WO | WO 01/12327 A1 | | 2/2001 | |
| WO | WO 01/89787 A2 | | 11/2001 | |
| WO | WO 01/94635 A2 | | 12/2001 | |
| WO | WO 02/068104 A1 | | 9/2002 | |
| WO | WO 2004/002627 A2 | | 1/2004 | |
| WO | WO 2004/091763 A2 | | 10/2004 | |
| WO | WO 2005/002730 A1 | | 1/2005 | |
| WO | WO 2005/021151 A1 | | 3/2005 | |
| WO | WO 2006/027757 A2 | | 3/2006 | |
| WO | WO 2007/133710 A2 | | 11/2007 | |
| WO | WO 2007123908 A2 | * | 11/2007 | ........... C07K 1/1136 |
| WO | WO 2009/050512 A2 | | 4/2009 | |
| WO | WO 2009/120254 A1 | | 10/2009 | |

OTHER PUBLICATIONS

Chinese Office Action for Application No. CN 201080035947.6 dated Mar. 4, 2014.
Extended European Search Report for Application No. EP 13165665.4 mailed Nov. 22, 2013.
Singaporean Examination Report for Application No. SG 201109630-2 dated Oct. 18, 2013.
Search Report and Written Opinion for Application No. SG 201109630-2 mailed Apr. 19, 2013.
Song et al., Reactions in droplets in microfluidic channels. Angew Chem Int Ed Engl. Nov. 13, 2006;45(44):7336-56.
Australian Examination Report for Application No. 2010266010 dated Feb. 4, 2015.
Australian Examination Report for Application No. 2010266010 dated Oct. 28, 2014.
U.S. Appl. No. 60/489,091, Link et al., Aug. 27, 2003.
U.S. Appl. No. 61/098,674, Weitz et al., Sep. 19, 2008.
International Search Report and Written Opinion for mailed Feb. 25, 2011.
International Preliminary Report on Patentability for PCT/US2010/040006 mailed Jan. 12, 2012.
Link et al., Electric control of droplets in microfluidic devices. Angew Chem Int Ed Engl. Apr. 10, 2006;45(16):2556-60.
Teh et al., Droplet microfluidics. Lab Chip. Feb. 2008;8(2):198-220. Epub Jan. 11, 2008.
Chinese Office Action for Application No. CN 201080035947.6 mailed Aug. 1, 2013.
Examination Report dated Aug. 13, 2014 for Application No. AU 2010266010.
Australian Office Action dated May 28, 2014 for Application No. 2010266010.
Japanese Office Action dated May 20, 2014 for Application No. 2012-517772.
Japanese Office Action dated Apr. 7, 2015 for Application No. 2012-517772.
Australian Office Action dated May 15, 2015 in connection with Application No. 2010266010.
European Office Action for Application No. 10792729.5 mailed Sep. 17, 2015.

* cited by examiner

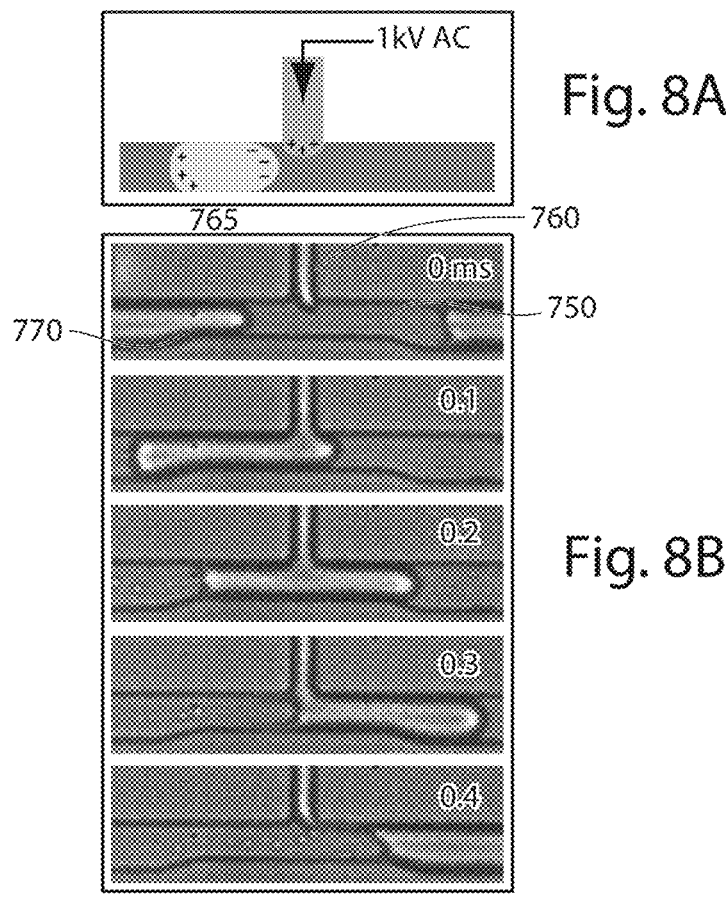
Fig. 8A
Fig. 8B
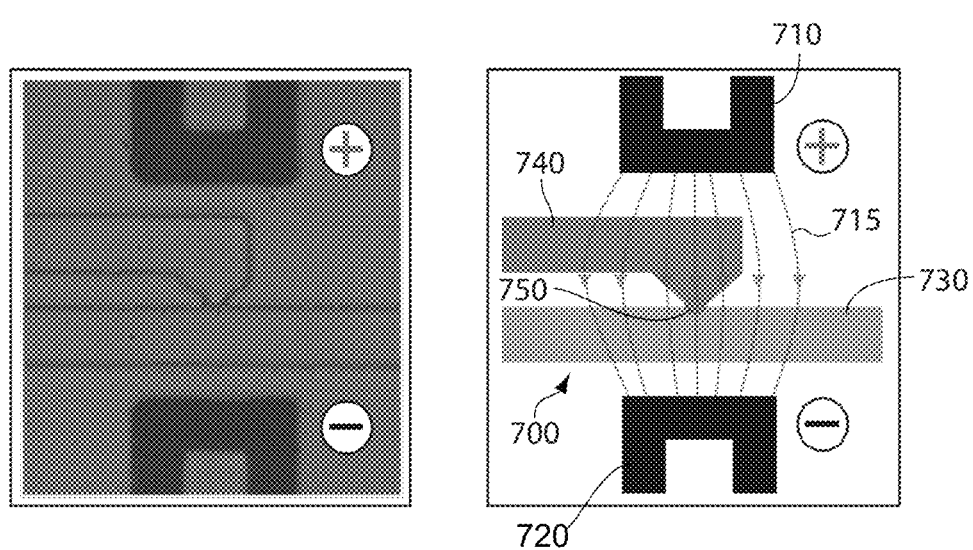
Fig. 9A
Fig. 9B

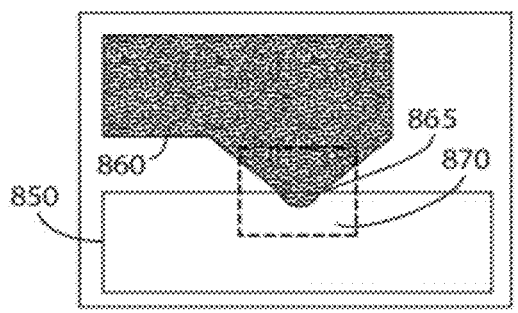
Fig. 12A
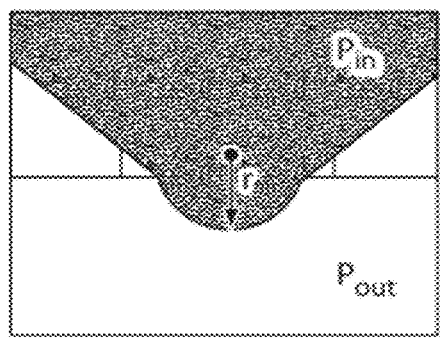
Fig. 12B
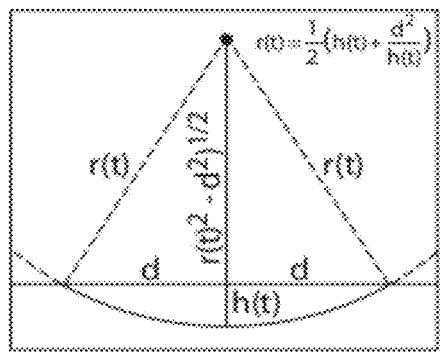
Fig. 12C
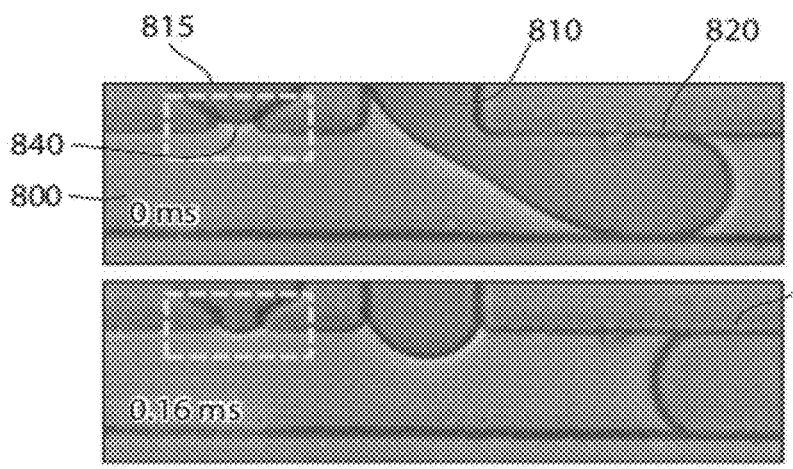
Fig. 13A
Fig. 13B

FLUID INJECTION

RELATED APPLICATIONS

This application claims the benefit of U.S. Provisional Patent Application Ser. No. 61/220,847, filed Jun. 26, 2009, entitled "Fluid Injection," by Weitz, et al., incorporated herein by reference.

FEDERALLY SPONSORED RESEARCH

This invention was made with government support under Grant Nos. DBI-0649865 and DMR-0820484 awarded by the National Science Foundation. The government has certain rights in the invention.

FIELD OF INVENTION

The present invention generally relates to systems and methods for the control of fluids and, in some cases, to systems and methods for flowing a fluid into and/or out of other fluids.

BACKGROUND

The manipulation of fluids to form fluid streams of desired configuration, discontinuous fluid streams, droplets, particles, dispersions, etc., for purposes of fluid delivery, product manufacture, analysis, and the like, is a relatively well-studied art. Droplet microfluidics are useful for a variety of purposes including high-throughput analysis of chemical and biological systems.

In many applications, several fluids must be combined in a specific sequence. Existing methods describe achieving this result by separately emulsifying a plurality of fluids as droplets, and bringing the droplets into contact at which point the droplets may be coalesced to combine the fluids. While droplet coalescence has been demonstrated for pairs of droplets, it is difficult to control.

SUMMARY OF THE INVENTION

The present invention generally relates to systems and methods for the control of fluidic droplets and, in some cases, to systems and methods for flowing a fluid into and/or out of other fluids. The subject matter of the present invention involves, in some cases, interrelated products, alternative solutions to a particular problem, and/or a plurality of different uses of one or more systems and/or articles.

In one aspect, a method is provided. The method, in this aspect, comprises providing a first fluid and a second fluid in contact with the first fluid at an interface, wherein the first fluid and the second fluid do not substantially mix, and wherein at least one of the first fluid and the second fluid is not a fluidic droplet contained within a carrying fluid. The method further comprises applying an electric field to the interface sufficient to disrupt at least a portion of the interface and flowing at least a portion of the second fluid into the first fluid.

In another aspect, a method is provided that comprises providing a first fluid and a second fluid in contact with the first fluid at an interface, wherein the first fluid and the second fluid do not substantially mix, and wherein at least one of the first fluid and the second fluid is not a fluidic droplet contained within a carrying fluid. The method further comprises applying an electric field to the interface sufficient to disrupt at least a portion of the interface and removing at least a portion of the second fluid into the first fluid.

In yet another aspect, a method is provided. The method, in this aspect, comprises applying an electric field to an interface defined between a first fluid and a second fluid contained within a channel and applying a pressure to the second fluid contained within the channel sufficient to cause at least a portion of the second fluid to enter the first fluid.

In one set of embodiments, the method includes acts of providing a microfluidic system comprising a first microfluidic channel and a second microfluidic channel contacting the first microfluidic channel at an intersection, providing a first fluid in the first microfluidic channel and a second fluid in the second microfluidic channel, and applying an electric field to the interface to urge the second fluid to enter the first microfluidic channel. In some cases, the first fluid and the second fluid may contact each other at least partially within the intersection to define a fluidic interface. In certain instances, in the absence of the electric field, the second fluid is not urged to enter the first microfluidic channel.

The method, in another set of embodiments, includes acts of providing a microfluidic system comprising a first microfluidic channel and a second microfluidic channel contacting the first microfluidic channel at an intersection, providing a first fluid in the first microfluidic channel and a second fluid in the second microfluidic channel, and applying an electric field to the interface to urge fluid from the first microfluidic channel into the second microfluidic channel. In some embodiments, the first fluid and the second fluid may contact each other at least partially within the intersection to define a fluidic interface. According to some embodiments, in the absence of the electric field, the first fluid is not urged to enter the second microfluidic channel In yet another set of embodiments, the method includes acts of providing a microfluidic system comprising a first microfluidic channel and a second microfluidic channel contacting the first microfluidic channel at an intersection, providing a first fluid in the first microfluidic channel and a second fluid in the second microfluidic channel, and urging the second fluid to enter the first microfluidic channel. The first fluid and the second fluid may contact each other at least partially within the intersection to define a fluidic interface, at least in some embodiments. In certain cases, when an electric field is applied to the interface, the second fluid may be at least partially prevented from entering the first microfluidic channel.

The method, in still another set of embodiments, includes acts of providing a microfluidic system comprising a first microfluidic channel and a second microfluidic channel contacting the first microfluidic channel at an intersection, providing a first fluid in the first microfluidic channel and a second fluid in the second microfluidic channel, and urging fluid from the first microfluidic channel into the second microfluidic channel. In some embodiments, the first fluid and the second fluid may contact each other at least partially within the intersection to define a fluidic interface. In certain embodiments, when an electric field is applied to the interface, the fluid can be at least partially prevented from entering the second microfluidic channel In still another aspect, a microfluidic apparatus is provided. The apparatus comprises, in one set of embodiments, a first fluidic channel, a second fluidic channel in fluidic communication with the first fluidic channel at an intersection, and first and second electrodes positioned on generally opposing sides of the first fluidic channel or the second fluidic channel, wherein the first fluidic channel, the second fluidic channel, the first electrode, and the second electrode are positioned such that a plane intersects each of these.

In another set of embodiments, the microfluidic apparatus includes a first microfluidic channel, a second microfluidic channel contacting the first microfluidic channel at an intersection, and first and second electrodes positioned on opposing sides of the first microfluidic channel and the second microfluidic channel. In some embodiments, the second microfluidic channel connects to the intersection via an orifice having an area of no more than about 90% of the average cross-sectional dimension of the second microfluidic channel.

The microfluidic apparatus includes, in yet another set of embodiments, a first microfluidic channel, a second microfluidic channel contacting the first microfluidic channel at an intersection, and first and second electrodes positioned on the same side of the first microfluidic channel. In certain cases, the second microfluidic channel connects to the intersection via an orifice having an area of no more than about 90% of the average cross-sectional dimension of the second microfluidic channel.

In yet another aspect, an article is provided. The article comprises, according to one set of embodiments, a microfluidic channel comprising a first plurality of droplets of a first droplet type and a second plurality of droplets of a second droplet type distinguishable from the first droplet type, the first and second droplet types defining a repeating pattern within the microfluidic channel that repeats at least twice and has a repeat unit that includes more than a single droplet.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more applications incorporated by reference include conflicting and/or inconsistent disclosure with respect to each other, then the later-filed application shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For the purposes of clarity, not every component is labeled in every figure, nor is every component of each embodiment of the invention shown where illustration is not necessary to allow those of ordinary skill in the art to understand the invention. In the figures:

FIGS. 8A-8B show fluid injection in accordance with another embodiment of the invention;

FIGS. 9A-9B show another embodiment of the invention for droplet injection;

FIGS. 12A-12C illustrate pressure measurements according to yet another embodiment of the invention; and FIGS. 13A-13B illustrate a sensor in still another embodiment of the invention.

DETAILED DESCRIPTION

The present invention generally relates to systems and methods for the control of fluids and, in some cases, to systems and methods for flowing a fluid into and/or out of other fluids. As examples, fluid may be injected into a droplet contained within a fluidic channel, or a fluid may be injected into a fluidic channel to create a droplet. In some embodiments, electrodes may be used to apply an electric field to one or more fluidic channels, e.g., proximate an intersection of at least two fluidic channels. For instance, a first fluid may be urged into and/or out of a second fluid, facilitated by the electric field. The electric field, in some cases, may disrupt an interface between a first fluid and at least one other fluid. Properties such as the volume, flow rate, etc. of a first fluid being urged into and/or out of a second fluid can be controlled by controlling various properties of the fluid and/or a fluidic droplet, for example curvature of the fluidic droplet, and/or controlling the applied electric field.

Figure 1:
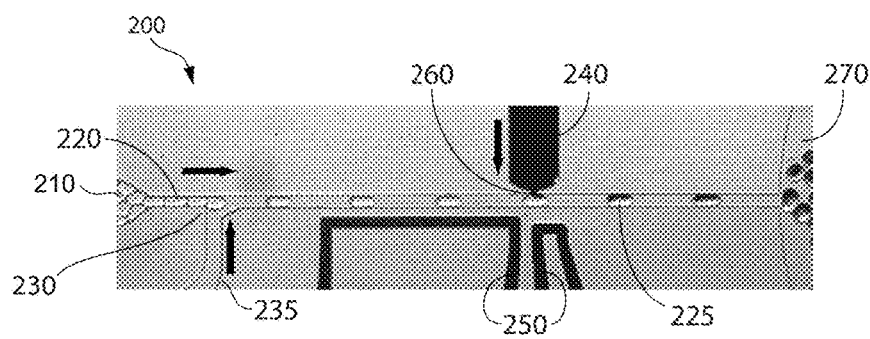
FIG. 1 shows a system for flowing fluid into and/or out of another fluid in accordance with an embodiment of the invention.

One illustrative example is now provided with reference to FIG. 1. It should be understood, however, that other embodiments besides the one illustrated in FIG. 1 are also contemplated in other embodiments of the invention, as discussed in detail below. In the example of FIG. 1, a system for flowing a first fluid (e.g., a fluid within a channel) into and/or out of a second fluid (e.g., a fluidic droplet) is illustrated. FIG. 1 shows system 200 having a droplet source 210 from which droplets 220 flow into first channel 230. Intersecting first channel 230 is fluid source 235, which is used to control the flow of droplets in first channel 230, e.g., using flow-focusing techniques or other techniques such as is described in more detail below. Also as shown in FIG. 1 are electrodes 250 and second channel 240, which intersects with first channel 230 at intersection 260. Electrodes 250 are positioned on one side of first channel 230 near intersection 260, and opposite second channel 240. As the droplets flow past intersection 260, a fluidic interface is formed between the droplets and an injectable fluid in second channel 240. Electrodes 250 create an electric field that may disrupt the interface between the droplet and the injectable fluid, thus allowing fluid to flow from the second channel into the droplet, thereby forming droplets 225. However, in the absence of an electric field, no disruption of the interface may occur, and thus, fluid from second channel 240 does not enter into droplets 220. Droplets 225 containing the injectable fluid subsequently leave intersection 260, e.g., flowing into collection channel 270.

In certain aspects of the invention, systems such as those described herein may be used to perform fluidic injections into and/or fluidic withdrawals from a fluid, for example, from a channel containing a fluid, from a fluidic droplet, or the like. As described in the example above, these operations may be performed on a first fluid by disrupting an interface defined between a first fluid and a second fluid. It should be understood that fluid injection and/or withdrawal may include only a portion of a fluid. In some cases, however, fluid exchange in both directions may occur; i.e., a portion of the first fluid may be injected into the second fluid while a portion of the second fluid may be withdrawn into the first fluid. Likewise, disruption of an interface may comprise disrupting a portion of the interface or the entire interface. It should also be understood that fluid exchange may comprise fluid injection into and/or withdrawal from a fluid, depending on the embodiment.

Accordingly, the invention, in some aspects, relates to systems and methods for fusing or coalescing two or more fluids into one fluid (e.g., fluid from a fluidic channel may be injected into a fluidic droplet). For instance, in one set of embodiments, two or more fluids may be fused or coalesced into one droplet in cases where the two or more fluids ordinarily are unable to fuse or coalesce, for example, due to composition, surface tension, droplet size, the presence or absence of surfactants, etc. For example, a fluid may be injected into one or more fluidic droplets. In certain microfluidic systems, the surface tension of the droplets, relative to the size of the droplets, may also prevent fusion or coalescence from occurring in some cases, absent the systems and methods disclosed herein for fusing or coalescing fluids. Additional examples of fusing or coalescing fluidic droplets are described in International Patent Application Serial No. PCT/US2004/010903, filed Apr. 9, 2004 by Link, et al., incorporated herein by reference.

Figure 5A:
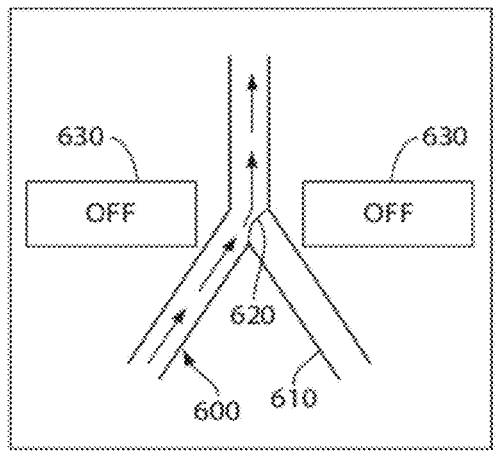
FIGS. 5A-5B show a system for flowing fluid into and/or out of another fluid in accordance with still another embodiment of the invention.
Figure 5B:
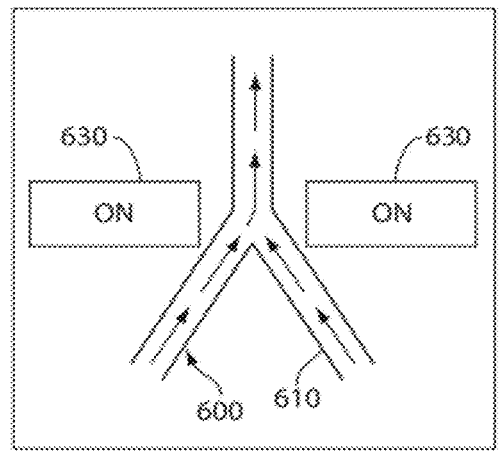

In some embodiments, a first channel is in fluid communication with a second channel at an intersection where the first channel and the second channel meet, e.g., as shown in FIG. 1. As shown in FIG. 1, the first channel may be designated as the "main" channel (channel 230) and the second channel may be designated as the "side channel" (channel 240). However, it should be understood that in other embodiments, other channel arrangements are possible, and that "main" and "side" channels are for explanatory purposes only. Generally, as used herein, the "main" channel and the "side" channel may each contain fluid, and the main channel is the channel in which fluid flows when an electric field is turned off, with the interface separating fluid in the main channel from fluid in the side channel, while the "side" channel holds fluid that flows when the interface is disrupted. Typically, the "main" channel for carrying a first fluid continues on past the intersection while the "side" channel for carrying a second fluid ends at the intersection, although the "main" channel need not be linear. However, the "main" and "side" channels need not have the T-arrangement shown in FIG. 1. In other embodiments of the invention, for example, the side channel may be aligned with an outlet channel, the various channels may be joined in a "Y" arrangement or in a 3-dimensional arrangement, or the like. A non-limiting example of a "Y" arrangement is shown in FIGS. 5A-5B.

In some cases, the first or main channel may have a cross-sectional area (i.e., defined perpendicular to fluid flow within the channel) that does not change substantially as the channel approaches the intersection. In other instances, however, the cross-sectional area may increase or decrease (i.e., constrict) as the first channel approaches the intersection. For example, the cross-sectional area of the first channel may decrease approaching the intersection.

The second channel may intersect the first channel at an intersection at any point along the first channel. At the point of intersection between the first channel and the second channel, the second channel may meet the first channel via an orifice in some embodiments, i.e., a portion of the second channel at the intersection with the first channel may have a cross-sectional area that is smaller than the cross-sectional area of the second channel leading up to the intersection. In other embodiments, however, no orifice may be present, or the cross-sectional area of the second channel may even be relatively larger in some cases. The orifice may be of any shape, for example circular, elliptical, triangular, rectangular, etc., and may be positioned in any suitable position in the second channel, e.g., at an end or on a side of the second channel, such as is shown in FIGS. 9A and 9B.

As described herein, the geometry of the intersection may affect fluid exchange between a fluid in the first channel and a fluid in the second channel. The orifice may have an average cross-sectional dimension less than about 100 microns, less than about 30 microns, less than about 10 microns, less than about 3 microns, less than about 1 micron, less than about 300 nm, less than about 100 nm, less than about 30 nm, less than about 10 nm, etc. In some cases, the orifice may have a cross-sectional area that is no more than about 90% of the average cross-sectional dimension of the channel, and in some cases, the area is no more than about 80%, no more than about 70%, no more than about 60%, no more than about 50%, no more than about 40%, no more than about 30%, no more than about 20%, or no more than about 10% of the average cross-sectional dimension of the channel. The orifice may be flush with an intersecting wall of the first channel (i.e., the orifice may be defined by a lack of a portion of a wall of the first channel). One non-limiting example is shown in FIG. 2. Alternatively, in some cases, the orifice may be in a position that protrudes into the first channel.

In some embodiments, one or more electrodes are provided that can apply an electric field to an intersection of a first channel and a second channel. In some cases, the electrodes may be positioned such that the electrodes create an electric field maximum that contains the intersection, or at least is proximate the intersection. For instance, the electrodes may be positioned to create an electric field or an electric field maximum located where the second channel intersects with the first channel, or such that the interface between two fluids in the channels experiences a suitable electric field. The electrodes may be positioned relative to the channels in a variety of configurations. In some examples, an electrode may be positioned essentially opposite a second channel. Alternatively, an electrode may be positioned substantially to one side of the second channel. In some embodiments, an electrode may be positioned above or below the second channel (e.g., in another layer of the device).

In some cases, a plurality of electrodes are provided. For example, two electrodes may be positioned essentially on the same or opposite sides of the first or second channels. In some instances, two electrodes may be positioned on opposite sides of both the first channel and second channel. An example of an embodiment in which the electrodes are positioned on the same side is shown in FIG. 1, while an embodiment in which the electrodes are positioned on opposite sides is shown in FIG. 9. In some embodiments, a first electrode and a second electrode may be positioned such that a plane intersects both electrodes. In some cases, the electrodes may be positioned to be co-planar with one or more channels (e.g., as shown in FIG. 1), e.g., such that the first fluidic channel, the second fluidic channel, and the electrodes are positioned such that a plane intersects each of these.

Referring again to FIG. 9, FIG. 9A shows a photomicrograph of an example system, while FIG. 9B is a schematic diagram of the same system. In this example, system 700 includes a first electrode 710, and an opposed, second electrode 720 that is co-planar with first electrode 710. In the example in FIG. 9B, during use, electrode 710 is positive, while electrode 720 is negative. However, in other embodiments, electrode 710 may be negative and electrode 720 may be positive. In this figure, electrodes 710 and 720 are positioned on opposite sides of intersection 750 between a first, main channel 730 and a second, side channel 740. The electrodes may be positioned such that the electric field created between the electrodes is centered over the intersection between first channel 730 and second channel 740, as is shown in FIG. 9B, or the electrodes may be positioned in an off-center configuration, in other embodiments of the invention. As shown here, electric field lines 715 are generated going from the positive electrode 710 to the negative electrode 720. Due the location of the electrodes, electric field lines 715 passing from electrode 710 to electrode 720 pass over intersection 750. Thus, by controlling the voltage between the electrodes, the electric field at intersection 750 may be controlled. Also shown in FIG. 9B, first channel 730 is filled with a first fluid, while second channel 740 is filled with a second fluid (shown here as a different shade for purposes of clarity). As discussed herein, the second fluid from second channel 740 may be injected into first channel 730, and/or into droplets (not shown) within the first channel 730.

An example of use of such a system is now discussed with reference to FIG. 8B. In this figure, fluid within a first channel 750 passes by fluid extending from second channel 760, and through the controlled application of an electric field (e.g., by electrodes, not shown in FIGS. 8A and 8B), a portion of the fluid from second channel 760 is injected into a droplet 770 contained within first channel 750 as droplet 770 passes through intersection 765 of first channel 750 with second channel 760. As previously discussed, the amount of fluid injected into the droplet may be controlled by controlling the strength of the electric field applied to the intersection, and/or other factors such as is described herein. For example, in one set of embodiments, if no electric field is applied via the electrodes, then no fluid injection may occur, or the volume of fluid that is injected into first channel 750 from second channel 760 may be controlled, at least in part, by controlling the electric field applied to the intersection.

An electrode as discussed herein may be fabricated from any suitable material, and if two or more electrodes are present, the electrodes may be formed from the same or different materials. Non-limiting examples of electrode materials include metals, metalloids, semiconductors, graphite, conducting polymers, and the like. The electrode may have any shape suitable for applying an electric field. In some cases, an electrode may have an essentially rectangular shape. As another example, an electrode may be elongated and have a tip defined as a region of the electrode closest to an intersection between a first channel and a second channel. In some embodiments, the tip of an electrode may have a width that is similar to a width of the second channel. In other embodiments, the tip of an electrode may have a width substantially larger than a width of the second channel. The electrode shape can be flat, V-shaped, or any other suitable shape, such as the shapes discussed herein.

In some cases, the tip of the electrode is constructed such that an electric field maximum is created, e.g., in the intersection or proximate the intersection, as previously discussed. For example, an electrode may be constructed such that the electric field gradient is optimized in the direction of the desired interface disruption. In some instances, e.g., where multiple electrodes are used (e.g., as discussed relative to FIG. 3 herein), the electrodes may be constructed to minimize interference between one or more electrodes and one or more channels; for example, by minimizing the unintended exposure of a first interface to an electric field by an electrode intended to expose a second interface positioned in a different location than the first interface to an electric field. In some embodiments, reducing the size of an electrode tip can allow more focused application of an electric field by the electrode tip such that one or more interfaces are not unintentionally exposed to the electric field, and/or are exposed to relatively lower electric field strengths. This may be advantageous, for example, in instances where it is desired to reduce the distance between a plurality of injection systems.

The electric field produced by the electrodes, in some embodiments, is generated using an electric field generator, i.e., a device or system able to create an electric field that can be applied to the fluid, e.g., via one or more electrodes. For example, the electric field generator may include a voltage source and one or more electrodes. Voltage sources include batteries, wall current, fuel cells, or the like, and a wide variety of voltage sources are commercially available. The electric field generator may produce an AC field (i.e., one that varies periodically with respect to time, for example, sinusoidally, sawtooth, square, etc.), a DC field (i.e., one that is constant with respect to time), a pulsed field, etc. The electric field generator may be constructed and arranged to create an electric field within a fluid contained within a channel or a microfluidic channel. The electric field generator may be integral to or separate from the fluidic system containing the channel, according to some embodiments. As used herein, "integral" means that portions of the components integral to each other are joined in such a way that the components cannot be manually separated from each other without cutting or breaking at least one of the components. In addition, in some cases, the electric field may be automatically controlled, e.g., by aid of a computer or an automatic device.

As mentioned, in some instances, the electric field is applied to an intersection between a first channel and a second channel; for example, the electric field may be applied to an intersection between a first channel and a second channel. The electric field may be applied continuously, periodically, or intermittently, depending on the embodiment, and may be AC, DC, etc. For example, while an intersection is exposed to an electric field, a fluidic droplet may be urged into or through the intersection. The electric field may be applied to disrupt the interface formed between the fluidic droplet and, for example, a fluid in the second channel, e.g., as discussed above, thereby allowing fluid exchange from the second channel into the first channel to occur. As another example, by controlling the electric field, fluid from the second channel may be urged into the first channel to create one or more new droplets contained within the first channel.

The voltage applied to the electrodes may be any suitable voltage for disrupting a fluidic interface. For example, the voltage may be between 0.1 V and 10,000 V, between 0.1 V and 1,000 V, between 0.1 V and 300 V, between 0.1 V and 100 V, between 0.1 V and 50 V, between 0.1 V and 30 V, between 0.1 V and 10 V, or the like. As applied voltage may be applied continuously, pulsatile, intermittently, randomly, etc. The pulses may be DC, or AC, with any suitable frequency, for example, frequencies in the hertz, kilohertz, or megahertz ranges, etc.

For example, in one embodiment, the electric field that is applied may be pulsed. For instance, the electric field may be applied when a fluidic droplet is present at an intersection, but not applied at other times. In another embodiment, the electric field is applied while a fluidic droplet is in front of the second channel. For example, the electric field may be applied for a period of time sufficient for injection and/or withdrawal of a specific volume of fluid, e.g., the electric field may on for a period of time and off for a period of time while the fluidic droplet is in front of the second channel.

By applying a voltage across the electrodes, e.g., via an electric field generator, an electric field may be created, which may be modeled as electric field lines passing from the positive electrode to the negative electrode, as is shown in FIG. 9B. The electric field lines may pass through the interface between the fluids, for example, in the same direction as the flow during injection of a fluid from the second channel into the first channel. Other angles may be used in other embodiments. The electrodes may be positioned to center the electric field over the intersection, or offset from the center, for example, to generate a component of the electric field in a direction of a flow channel.

In some aspects of the invention, as described, techniques for injecting and/or withdrawing a first fluid from a second fluid involve formation of an interface between the first fluid and the second fluid, disruption of the interface (e.g., using an electric field) such that it does not present a barrier between the first and second fluids, and allows transfer of fluid between the first fluid and the second fluid. For instance, when an interface between a first fluid and a second fluid (e.g., between a fluid within a second channel and a droplet in a first channel positioned at an intersection with the second channel) is disrupted, fluid may flow from the first fluid to the second fluid, from the second fluid to the first fluid, or both (e.g., through diffusion or convection of the two fluids with respect to each other). As an example, by controlling the difference in pressures between the first and second channels, fluid may be urged to flow preferentially in one direction or another (e.g., towards the droplet, i.e., injection, or away from the droplet, i.e., withdrawal).

Thus, in certain cases, at least a portion of an interface between two fluids may be disrupted to allow fluid flow between the two fluids to occur. In some embodiments, at least a portion of the interface may be disrupted by electric field, e.g., applied by using electrodes such as those described herein. The electric field may be, for example, an AC field, a DC field, a pulsed field, etc.

Without wishing to be bound by any theory, it is believed that application of an electric field causes forces that are acting to disrupt the interface (e.g., shear forces, mechanical forces, electrical forces such as Coulombic forces, etc.) to become larger than forces acting to maintain the interface (e.g., surface tension, surfactant molecule alignment and/or steric hindrance, etc.). For example, one possible mechanism by which the electric field disrupts the fluidic interface is that dipole-dipole interactions induced by the electric field in each of the fluids may cause the fluids to become electrically attracted towards each other due to their local opposite charges, thus disrupting at least a portion of the interface and thereby causing a fluidic connection to form between the fluids, which may be used for injection, withdrawal, mixing, or the like. Another possible mechanism by which the electric field disrupts the interface is that the electric field may produce a force directly on the fluids, thereby resulting in coalescence.

For instance, in one set embodiments, the fluid to be injected into a channel may be charged directly, for example, by application of an electric field using electrodes positioned to apply the electric field to or proximate the intersection. As a specific example, as a droplet within a first channel approaches the intersection of the first channel with the second channel, the droplet may at least partially polarize, e.g., as is depicted in FIG. 8A. The polarization may generate an attractive force between the fluids, which may cause them to become attracted to each other, and to merge in some instances. In some cases, the fluids may be at least partially conducting, and the fluids may be surrounded or contained within an insulating fluid, for example, oil, which may allow the fluids to exhibit charge or charge separation within the applied electric field.

In some embodiments, the fluidic interface may be disrupted after a certain threshold electric field strength has been reached. The threshold electric field strength may be any minimum value able to disrupt the interface, and may vary by application. For example, factors such as the viscosity or density of the fluids contained within the channel, the flow rate of fluids within the channels, the geometry (e.g., sizes or dimensions) of the channels, the angle at which the channels meet at an intersection, the presence of other forces applied to the fluid, etc., may affect the threshold electric field strength for a particular application. Non-limiting examples of electric field strength for disrupting an interface include electric field strengths greater than about 0.01 V/micrometer, greater than about 0.03 V/micrometer, greater than about 0.1 V/micrometer, greater than about 0.3 V/micrometer, greater than about 1 V/micrometer, greater than about 3 V/micrometer, greater than about 10 V/micrometer, etc. It should be understood that values outside these ranges may also be used in some instances. In some cases, the amount of fluid transfer may be essentially constant as a function of voltage above the threshold voltage. In other embodiments, the amount of interface disruption generally increases as electric field strength increases.

Non-limiting example of control and disruption of the interface follows. In general, control of the interface depends on factors such as the nature of the fluids within the channels (e.g., their viscosity or density), the curvature of the fluids at the fluidic interface, the size of the channels (which affects their curvature at the interface), the size of the intersection of the channels, or the like. An example of the control and disruption of an interface between two fluids is now described with reference to a system having a first channel and a second channel that meet at an intersection, where the first ("main") channel carries a fluidic droplet and a second ("side") channel carries a fluid to be injected into the fluidic droplet, and/or is used to withdraw fluid from the fluidic channel.

As one non-limiting example, a fluidic droplet in a first channel may form a fluidic interface with a fluid in a second channel, e.g., when the first channel and the second channel meet at an intersection. In some cases, the fluidic droplet in the first channel may be sufficiently large that the fluidic droplet is in contact with the walls of the first channel; in some cases, the width of the first channel may affect the radius of curvature of the fluidic droplet. The radius of curvature of fluid in the second channel at the interface of the fluid with the first channel may be controlled at least in part, in certain embodiments, by the cross-sectional area of the second channel at the intersection with the first channel (e.g., at an orifice or nozzle of the second channel, if one is present, as it contacts the first channel). That is, as the cross-sectional area of an orifice or intersection between the first and second channels decreases, the radius of curvature of the fluid in the second channel as it contacts the fluid in the first channel decreases. In some cases, the radius of curvature of the fluid in the second channel may be defined, at least in part, by pressurizing the fluid within the second channel such that the fluid at least partially protrudes from the orifice or interface into the first channel.

Figure 2A:
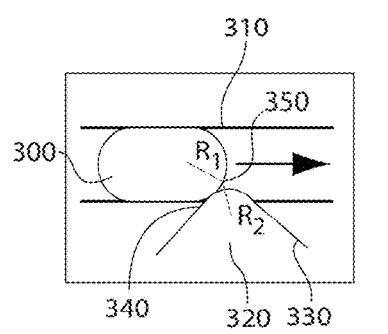
FIGS. 2A, 2B, and 2C show a droplet before injection, during injection, and after injection in accordance with another embodiment of the invention.

As a non-limiting example of this, referring to FIG. 2A, fluidic droplet 300 is shown in first channel 310 flowing from left to right in the figure. Fluid 320 is also shown in this example protruding from a second channel 330, where the second channel has orifice 340. It should be noted that, as is shown in FIG. 2, the orifice is at the end of a tapered portion of second channel 330; the orifice need not have the same size or average diameter as the fluidic channel flowing into the orifice. In this example, the radius of curvature $R_1$ of the fluidic droplet contained within first channel 310 is larger than the radius of curvature $R_2$ of the fluid entering first channel 310 from second channel 330. The fluidic droplet and fluid are thus in contact with each other forming an interface 350, as is shown in FIG. 2A.

Figure 2B:
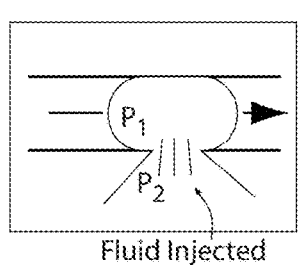

In FIG. 2B, the interface between the fluidic droplet and the entering fluid may be disrupted by exposure of the interface to a suitable electric field, as is discussed herein. It is believed, without wishing to be bound by any theory, that application of an electric field may alter the dipole moments of the fluids at the interface between the fluids, which may be at least sufficient to break the surface tension of the interface separating the fluids, thereby disrupting the interface separating the fluids and allowing fluid exchange to occur. In some cases, as discussed herein, the size and/or shape of the interface may also be controlled by controlling the electric field at the interface between the fluids; for example, stronger electric fields may increase alteration of the dipole moments of the fluids at the interface between the fluids, which may thereby alter the amount of disruption, the threshold of disruption, and/or the amount of fluid able to be exchanged between the fluidic droplet and the entering fluid. It should also be noted that fluidic droplet 300 is used by way of example only; in other embodiments, fluid from second channel 330 may be injected directly into first channel 310, i.e., without the presence of fluidic droplet 300 within first channel 310. In some cases, this may cause the creation of new fluidic droplets within the first channel.

The direction of fluid exchange between the fluidic droplet and fluid from second channel 330 may be controlled, according to various embodiments of the invention, by controlling factors such as the fluidic pressures of the various fluids, the strength of the electric field, the shape of the channel, the nature of the channel intersection, or the like. As a specific non-limiting example, in some cases, fluidic exchange may be controlled by controlling the pressures or relative pressures of the fluids. For instance, and without wishing to be bound by any theory, it is believed that by controlling the radii of curvature of the fluids such that $R_1$ (in the first channel) is greater than $R_2$ (in the second channel), for instance by controlling the pressure of the fluidic droplet ($p_1$) to be less than the pressure of the fluid in the second channel ($p_2$), fluid may flow from the second channel into the fluidic droplet. Thus, the fluid in the second channel can flow or be "injected" into the fluidic droplet after disruption of the interface in this example. In other cases, however, e.g., as discussed below, the pressures may be controlled such that $R_2$ is greater than $R_1$, and fluid may instead be withdrawn from the fluidic droplet into the second channel.

Figures 10A, 10B:
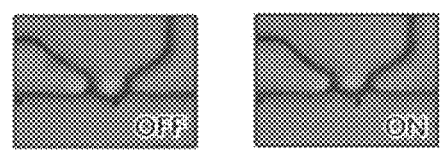
FIGS. 10A-10D illustrate electronic control of fluid injection in accordance with yet another embodiment of the invention.

As mentioned, the interface between the fluids may be controlled by controlling the pressure (or relative pressure) and/or the electric field applied to the interface. In certain embodiments, control of the electric field may afford electronic control of the interface, e.g., whether or when to control injection and/or withdraw of fluid into a channel and/or into a fluidic droplet within a channel. For example, by modulating the electric field, the position of the interface between the two fluids may be adjusted. As an example, the position of the interface may be relatively higher when an electric field is applied, as is shown in FIG. 10B, compared to when there is no electric field (or a weaker electric field), as is shown in FIG. 10A. The position of the interface may also be controlled dynamically in some embodiments, for example, by controlling the voltage applied to the electrodes.

Figure 10C:
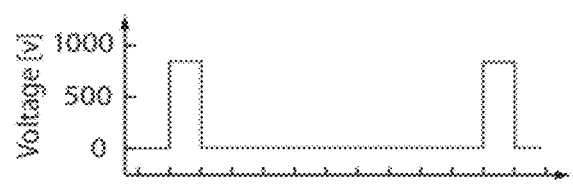
Figure 10D:
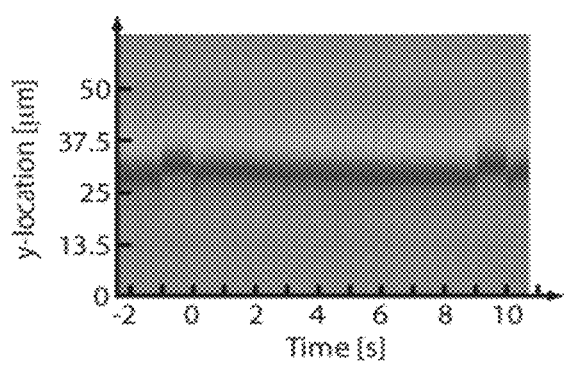

As a specific non-limiting example, referring now to FIG. 10C, when the voltage applied to the electrodes is adjusted, thereby adjusting the strength of the electric field created between the electrodes that is applied to the fluidic interface, the location of the interface responds correspondingly, as is shown in FIG. 10D (showing the position of the interface in this non-limiting example). (It should be noted that both FIGS. 10C and 10D are on the same time scale). Thus, by controlling the electric field applied to the interface, the position of the interface can likewise be controlled. As mentioned, in some embodiments, the electric field may be controlled by controlling the voltage applied to the electrodes disposed about the interface, e.g., via controlling the intensity or polarity of the voltage, and/or (e.g., if AC), controlling the amplitude, frequency, etc. of the voltage. For instance, by using higher voltages, the interface between the fluids may be extended farther into the first channel, allowing a larger volume to be injected into a fluidic droplet, whereas a smaller voltage may be used to cause the interface to extend less far into the channel, causing a lesser amount of fluid to be injected into the droplet. The interface position can also be modulated, in some embodiments, at suitable frequencies, for example, at frequencies that are comparable to the rate of droplet formation or passage by the interface, thereby allowing the amount of volume to be injected into each droplet to be individually controlled.

Figures 11A, 11B, 11C:
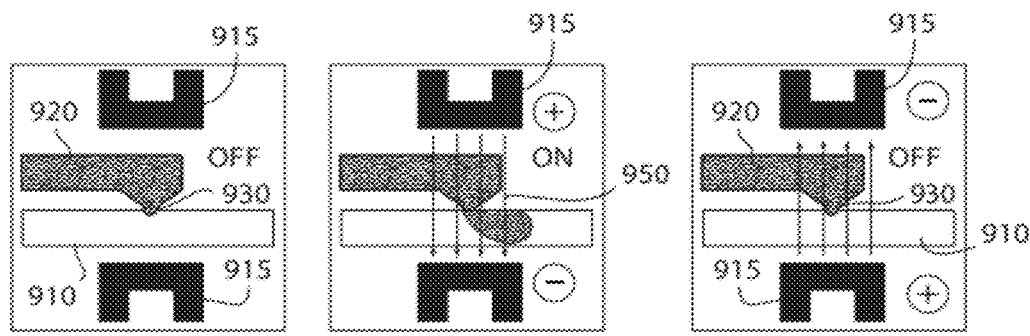
FIGS. 11A-11C illustrate droplet creation in accordance with still another embodiment of the invention.

In addition, in certain embodiments, if the electric field is increased or controlled sufficiently, the fluidic interface may be extended into a first channel so far that the fluid from a second channel breaks off into the first channel to form a new droplet. An example of this process is discussed with reference to FIGS. 11A and 11B. In FIG. 11A, when no electric field (or an insufficient electric field) is applied to an interface 930 created at an intersection between first channel 910 and second channel 920, the interface between a fluid within the second channel and fluid within the first channel is not disrupted, and thus, fluid within the second channel does not readily flow into the first channel, i.e., droplet creation is "off." However, in FIG. 11B, under an applied electric field (represented by electric field lines 950) created using electrodes 915, the interface between the fluids can be extended into the first channel.

Under suitable conditions (for example, a relatively rapid rate of fluid flow within the first channel), interface 930 may be extended quite far into first channel 910, e.g., as is shown in FIG. 11B. In some cases, the interface extends so far that the interface is disrupted, causing some fluid within second channel 920 to enter first channel 910 as a discrete droplet. Repeating this process may be used to create a plurality of fluidic droplets within first channel 910. It should be noted that, since this process is controlled electronically, rapid droplet production may be achieved in some cases. For instance, at least about 10 droplets per second may be created in some cases, and in other cases, at least about 20 droplets per second, at least about 30 droplets per second, at least about 100 droplets per second, at least about 200 droplets per second, at least about 300 droplets per second, at least about 500 droplets per second, at least about 750 droplets per second, at least about 1000 droplets per second, at least about 1500 droplets per second, at least about 2000 droplets per second, at least about 3000 droplets per second, at least about 5000 droplets per second, at least about 7500 droplets per second, at least about 10,000 droplets per second or more droplets per second may be created in such a fashion. Accordingly, in some embodiments, by controlling the electric field, individual fluidic droplets may be created within a channel. In addition, by adjusting factors such as the voltage, flow rates, and/or pressures within the fluids, the volume of the droplet thus formed within the channel may be controlled.

In another set of embodiments, the use of the electric field may be reversed, where the application is used to turn off or decrease droplet creation, instead of being used to create droplets. For example, in some cases, a fluidic droplet system such as those discussed herein may be used to create droplets. The fluidic droplet system may create droplets, e.g., using flow-focusing techniques or other techniques such as disclosed herein. When no electric field is applied, droplets may be formed; however, when a sufficient electric field is applied, e.g., using electrodes, the fluidic interface may be contracted, which may alter or inhibit droplet formation.

For example, in FIG. 11C, at an interface between a first fluid within first channel 910 and a second fluid within second channel 920, droplets may be created in the absence of an electric field, e.g., due to motion or pressures within the second channel that urge the second fluid into the first channel, e.g., forming droplets (for example, if the first and second fluids are substantially immiscible). However, upon the application of suitable electric field, as is shown in this figure with electric field lines 950 between electrodes 915, the applied electric field cause interface 930 between first channel 910 and second channel 920 to move; in this case, the interface moves "upstream" into second channel 920 and away from first channel 910, thereby slowing or inhibiting droplet formation of the second fluid into the first fluid within first channel 910. Accordingly, in another set of embodiments, the application of an electric field may be used to partially or completely prevent the second fluid from entering the first fluid. In addition, an analogous system may be used to prevent fluid from the first channel from being withdrawn into the second channel; i.e., in the absence of an electric field (or an insufficient electric field), fluid may be withdrawn into the second channel from the first channel, but upon application of a suitable electric field, the interface between the fluids moves such that fluid cannot be withdrawn into the second channel from the first channel.

In some aspects, fluid may be injected into a fluidic channel, e.g., in a fluidic droplet contained within the channel, which may in some cases cause mixing of the injected fluid with other fluids within the fluidic droplet to occur. The present invention broadly contemplates, in certain embodiments, various systems and methods for injecting fluid, e.g., into a fluidic droplet. It should be understood that, in the descriptions herein involving the "injection" of a fluid from a second channel into a first channel, the fluid that is injected may be injected into a droplet contained within the first channel and/or into fluid contained within the first channel, e.g., forming a new droplet. Thus, in some embodiments, fluid injection using a first channel, a second channel, and electrodes as discussed herein may be used to create new droplets of a fluid from the second channel that are individually contained within fluid within the first channel.

For example, in one set of embodiments, the fluid may be injected into the fluidic droplet using a needle such as a microneedle, a nozzle, an orifice, a tube, or other such devices. In another set of embodiments, the fluid may be injected directly into a fluidic droplet using a fluidic channel as the fluidic droplet comes into contact with the fluidic channel. For instance, in certain embodiments, a first channel containing a fluid may be intersected by a second channel at an intersection. Fluid from the second channel may be injected into the first channel, for example, using suitable pressures within one or both of the channels, e.g., a pump. For example, when a droplet contained within the first channel passes through the intersection, fluid from the second channel may be urged into the intersection, thereby entering the droplet and causing injection of fluid from the second channel into the droplet to occur.

Figure 2C:
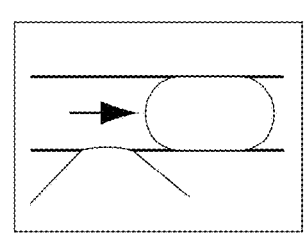

The amount of fluid injected can be controlled, in certain embodiments, by controlling properties such as the relative pressure of the fluids, the residence time of a droplet in the intersection, the viscosity of the fluids, the electric field applied to the interface, etc. For example, referring now to FIGS. 2B and 2C, fluidic droplet 300 is in fluidic communication with fluid from a second channel 330, and thus fluid can flow from second channel 330 into droplet 300. However, as fluidic droplet 300 moves through first channel 310, shear between fluidic droplet 300 and fluid from second channel 330 increases, and may cause the fluidic droplet to detach from the second channel 330 (FIG. 2C). In some cases, the interface between the fluid in first channel 310 and the fluid in second channel 330 may be restored by the shearing action of droplet flow past the intersection, as is shown in FIG. 2C.

The volume of fluid that may be injected and/or withdrawn may be any suitable amount, depending on the embodiment. For instance, the volume injected and/or withdrawn may be less than about 10 microliters, less than about 1 microliter, less than about 100 nanoliters, less than about 10 nanoliters, less than about 1 nanoliter, less than about 100 picoliters, less than about 10 picoliters, less than about 1 picoliter, etc. In some cases, fluid may be injected and/or withdrawn while the fluid in the first channel is in motion (i.e., flowing through a first channel). In other cases, fluid may be injected and/or withdrawn while the fluid in the first channel is held stationary. For example, pressure in the first channel may be controlled such that a droplet is urged to an intersection between the first channel and a second channel. The pressure and/or fluid flow within the first channel may then be decreased such that the droplet is then held stationary at the intersection, thereby allowing a desired amount of fluid to be injected and/or withdrawn into the droplet. The pressure may then be increased and/or fluid flow may be controlled to urge the droplet away from the intersection once a desired amount of fluid has been transported.

In some instances, the second channel may be configured, e.g., with a pump or other pressure control device such that fluid can be forcibly injected and/or withdrawn from the first channel, e.g., to or from a fluidic droplet, for example, without reliance on a difference in radii of curvature of the interface, or the like.

The flow velocity of the fluidic droplet within the first channel may be determined in some embodiments by factors such as the pressure or the pressure difference between the fluidic droplet in the first channel and the fluid in the second channel, the fluid pressure in one or both channels, the size of the orifice between the first channel and the second channel, the angle of intersection between the first and second channels, etc. as discussed above. The fluid pressure may be controlled using any suitable technique, for example, using a pump, siphon pressure, or the like.

As mentioned, the volume of fluid injected and/or withdrawn may be controlled using any suitable technique, for example, by controlling the pressures of the various fluids, the volumetric flow rates, the strength of the applied electric field, or the like. For instance, in some embodiments, the flow rate of fluid in the first channel can be used to control the volume of fluid injected and/or withdrawn. It is believed that this can be controlled since the flow rate of fluid in the first channel controls the flow rate of fluidic droplets in the first channel, which thereby controls the amount of time that the fluidic droplets are present at the intersection and/or exposed to fluid in the second channel.

In another set of embodiments, the pressure and/or the different in pressures between the fluids may be used to control the volume of fluid injected and/or withdrawn. For example, by equalizing the pressures, flow between the fluids may be minimized, while fluid may be urged to flow into or from a droplet or a channel by a suitable difference in pressures between the fluids. For example, the pressure in the second channel may be increased, relative to the first channel, to cause fluid flow to occur into the first channel, e.g., into a droplet within the first channel.

In some embodiments, the volume of fluid exchanged between two fluids may be controlled by controlling the residence time of a first fluid in proximity to a second fluid, e.g., by controlling the residence time of a fluid in the first channel and positioned in front of a second channel. As a non-limiting example, the residence time of a fluidic in a droplet in the first channel positioned in front of the second channel may be controlled by varying the flow rate of fluid in the first channel. That is, a longer residence time may be achieved by slowing the flow rate or even stopping the flow of the fluid in the first channel, relative to the second channel. Likewise, a shorter residence time may be achieved by increasing the flow rate of the fluid in the first channel.

In another set of embodiments, the duration of the electric field applied, e.g., while a droplet is positioned in an intersection of first and second channels may by varied. For example, to allow more fluid to exchange between fluid in the first channel and in the second channel, the interface may be disrupted for a longer period of time. To allow a smaller amount of fluid exchange, the interface may be disrupted for a shorter period of time.

In one set of embodiments, the systems and methods described herein may be used to transfer fluid between a first channel and a second channel. For example, a first fluid in a first channel may form an interface with a second fluid in a second channel. Disruption of the interface between the first fluid and the second fluid may allow fluid to be exchanged between the two fluids, as shown in FIGS. 5A-5B. In FIG. 5A, a first channel 600 containing a first fluid (the direction of flow is indicated by the arrows in the channel) is connected to a second channel 610 having a second fluid that is stationary. The two fluids are separated by an interface 620 when electrodes 630 are in the "OFF" state (or otherwise are at a voltage insufficient to disrupt interface 620). In FIG. 5B, electrodes 630 are in the "ON" state (i.e., at a voltage at least sufficient to disrupt interface 620), thereby causing disruption of interface 620 and allowing the second fluid in second channel 610 to flow into first channel 600. In some cases, the flow of fluid between the two channels may be facilitated, for example, by applying pressure to the first or second channel, reducing pressure on the first or second channel etc. As described above, the interface may be disrupted using methods such as exposure of the interface to an electric field.

As another example, the geometry of a second channel intersecting a first channel, in some cases, may influence fluid injection and/or withdrawal. Without wishing to be bound by any theory, it is believed that such control may be achieved since the flow velocity of the fluid in the second channel into a fluidic droplet is generally inversely related to the hydrodynamic resistance of the second channel. This property may be dominated, in some instances, by the narrowest constriction of the second channel. The flow velocity may be controlled, for example, by selecting appropriate channel dimensions and/or by controlling the pressures of the fluids within the channel. In some embodiments, for instance, the flow velocity may be less than about 1 mm/second, less than about 100 microns/second, less than about 10 microns/second, less than about 1 micron/second, less than about 100 nm/second, less than about 10 nm/second, less than about 1 nm/second, etc.

In certain embodiments, as mentioned, a second channel may be used for withdrawing fluid from a fluid in a first channel to which the second channel intersects. In some cases, the fluid in the first channel may be controlled to have a higher pressure than the fluid within the second channel. This may be accomplished in a variety of ways. In some instances, for example, the radii of curvature of a fluidic droplet in the first channel and a fluid in the second channel may be controlled such that the radius of curvature of the fluidic droplet is smaller than the radius of curvature of the fluid in the second channel that interfaces with the first channel. For example, the fluidic droplet may be controlled within the first channel resulting in a fluidic droplet with a smaller radius of curvature. In another embodiment, the cross-sectional area of the second channel (or the cross-sectional area of an orifice of the second channel) may be increased such that the radius of curvature of fluid emerging from the second channel into the first channel is larger, relative to a droplet in the first channel.

In some cases, the interior of a channel may be modified to change the wettability of the channel. For example, a channel such as a second channel may be modified such that the fluid emerging from the second channel into a first channel can adopt negative curvature inside the second channel (i.e., a concave configuration, concave being defined as withdrawn into the second channel as opposed to protruding from the second channel into the first channel). In such instances, for example, the second channel may be able to withdraw fluid rapidly from a fluid in the first channel, e.g., a droplet contained within the first channel. Examples of techniques for controlling or altering the hydrophilicity or hydrophobicity of a surface are disclosed in International Patent Application No. PCT/US2009/000850, filed Feb. 11, 2009, entitled "Surfaces, Including Microfluidic Channels, With Controlled Wetting Properties," by Abate, et al., incorporated herein by reference in its entirety.

Figure 3:
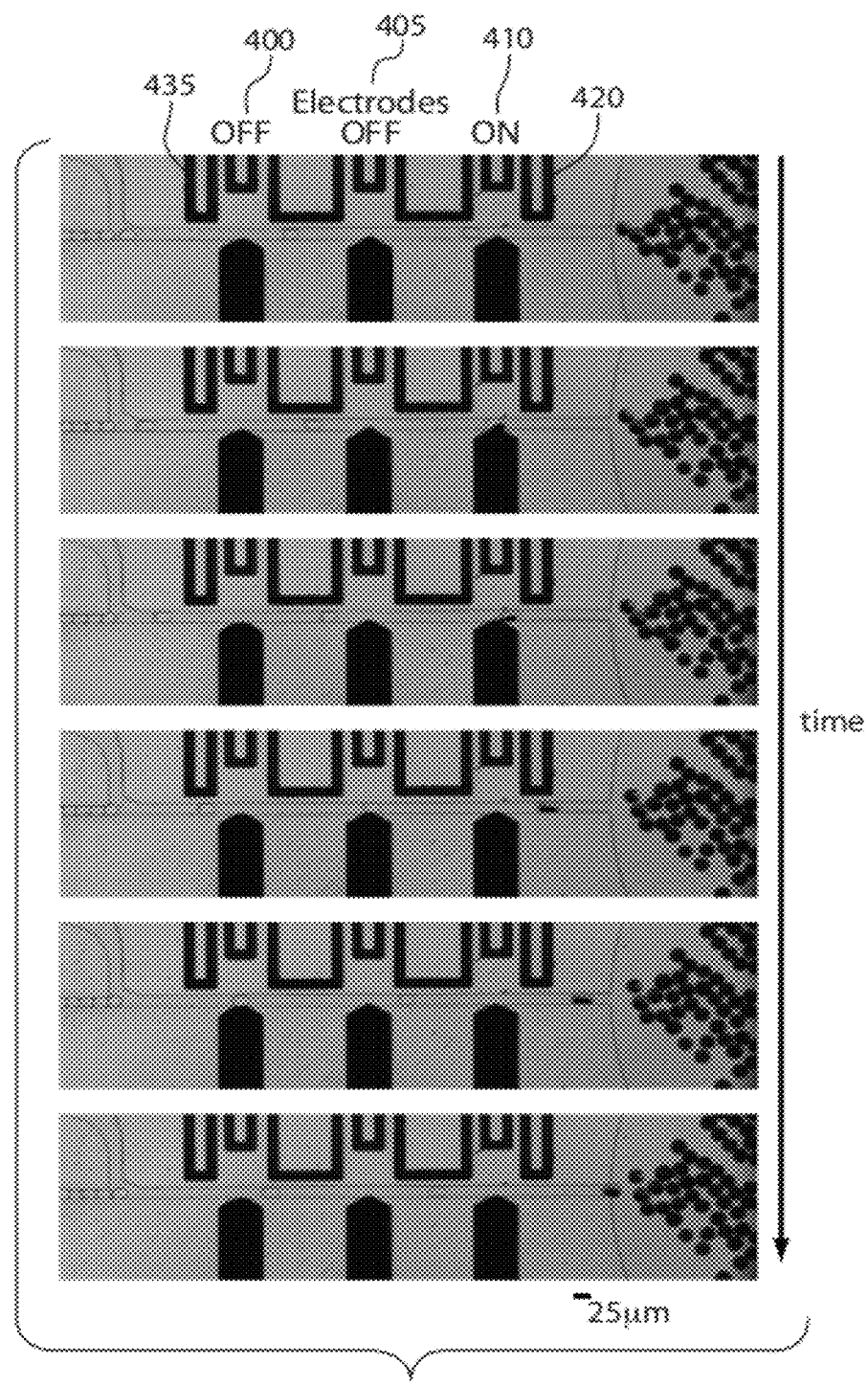
FIG. 3 shows a system for flowing fluid into and/or out of another fluid in accordance with yet another embodiment of the invention.

In some embodiments, a system may include multiple channels and/or electrodes. Such a system, for example, may be used to perform multiple injection/withdrawal operations, e.g., in series. For instance, FIG. 3 depicts a time sequence demonstrating injection of fluids into a fluidic droplet. In this figure, a plurality of injection systems are arranged in series. Each of the injection systems may contain the same, or a different fluid to be injected into a channel. For example, in certain instances, a single fluidic droplet may be injected with a plurality of different fluids as it flows through a channel, e.g., by use of a plurality of injection systems. As another example, in some embodiments, a first set of fluidic droplets may be injected with a first fluid and a second set of fluidic droplets may be injected with a second fluid.

As a specific non-limiting example, FIG. 3 shows electrodes 400, 405, and 410, with electrodes 400 and 405 in the "off" state (e.g., zero electric field, or an electric field that is below a threshold level at least sufficient to disrupt an interface). Electrode 410 is in the "on" state, applying an electric field sufficient to disrupt an interface. A fluidic droplet 420, having moved past channels 430 and 432 containing a colored fluid, has not been injected with colored fluid since electrodes 400 and 405, which can apply an electric field at the intersection of channel 435 and channels 430 and 432, respectively, are in the "off" state. Fluidic droplet 420 is, however, injected with colored fluid from channel 434 while at the intersection of channel 435 and channel 434 since electrode 410 is in the "on" state.

Other arrangements for performing multiple injections will be apparent to those skilled in the art. Multiple injections may be used to generate, for example, a combinatorial library of fluidic droplets, where each fluidic droplet has a unique combination of injections differentiated by properties such as injection content, injection amount (i.e., concentration, volume, etc.), time of injection (i.e., at different periods of time), etc.

Another aspect of the invention generally relates to a plurality of droplet types contained within a channel, such as a microfluidic channel. By using systems such as those described herein, droplets may be controlled within a channel to be distinguishable, for instance, on the basis of color, size, a species contained within some of the droplets, or the like. Thus, as a specific example, some droplets of a plurality of droplets may be injected to create a first plurality of droplets of a first droplet type and a second plurality of droplets of a second droplet type distinguishable from the first droplet type, for instance, by using a dye. Other examples of potentially suitable distinguishing characteristics include composition, concentration, density, etc.; optical properties such as transparency, opacity, refractive index, etc.; or electrical properties such as capacitance, conductance, resistivity, etc.

Figure 4A:
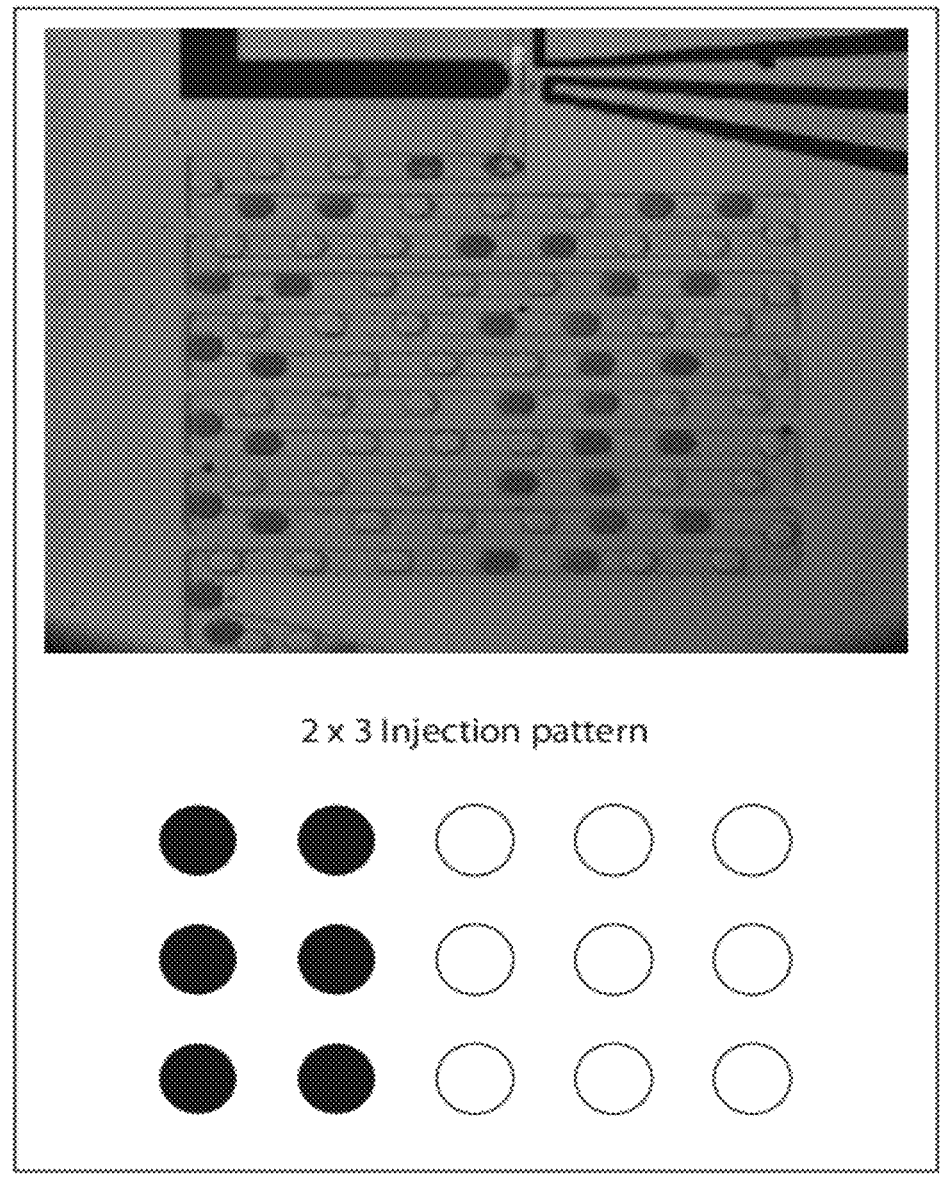
FIGS. 4A-4B illustrate various embodiments of the invention comprising patterns of droplets of a first fluid and of a second fluid in accordance with yet another embodiment of the invention.
Figure 4B:
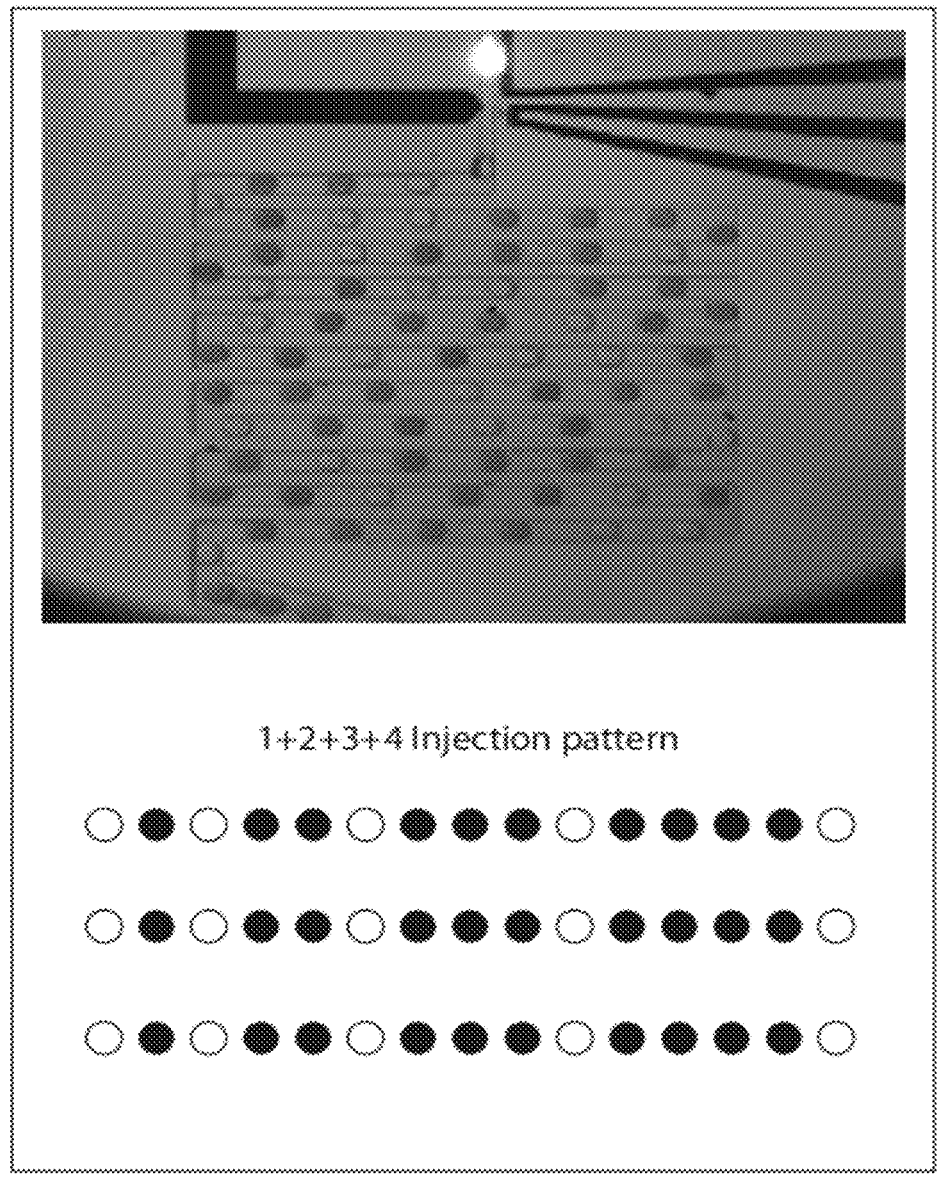

In one set of embodiments, using the systems and methods described herein, any arbitrary pattern of droplets within a channel may be injected, e.g., arbitrary, random, encoding a repeating sequence, or the like. For instance, the droplets may be injected in an alternating fashion (e.g., between first and second droplet types), or as is shown in FIGS. 4A and 4B, the fluidic droplets may be injected in longer repeating or arbitrary patterns, containing any number of droplets within a repeat unit (which is repeated at least twice within the channel to produce the repeating pattern), e.g., repeat units of 2, 3, 4, 5, 6, 7, 8, 9, 10, 12, 15, 20, etc., or more droplets. For instance, FIG. 4A illustrates an embodiment where two adjacent droplets are injected with a dye, followed by three adjacent droplets not injected with a dye, thereby creating a 5-droplet repeat unit; in FIG. 4B, a 15-droplet repeat unit is illustrated.

In addition, more complex sequences of droplets may be created in a channel, according to certain embodiments, by using more than two types of droplets. For instance, a channel may contain multiple sites of injection, e.g., as previously discussed, and injections may be controlled to create a first plurality of droplets of a first droplet type, a second plurality of droplets of a second droplet type, and a third plurality of droplets of a third droplet type. Even more droplet types may be created in other embodiments, e.g., fourth, fifth, sixth, etc. The droplets may be arranged in any suitable pattern, including arbitrary, random, or repeating patterns (which may have any number of droplets defining the repeat unit of the repeating pattern).

In another aspect, the pressure within a channel may be determined using a system such as those described herein. For example, by determining the balance of fluids between a first channel and a second channel, the pressure or pressure difference between the channels may be determined. The size or shape of the fluid interface between a first fluid in a first channel and a second fluid in a second channel is a function, at least in part, of the difference in pressure between the channels. By determining a property of the interface, e.g., by determining a radius of curvature of the interface, pressures within the channels on either side of the interface may be determined.

As a specific example, a first channel and a second channel may intersect at an intersection. The first channel may contain a first, continuous liquid. When fluid from the second channel enters the first channel at the intersection, a fluidic interface may be formed. The pressure within the continuous phase may fluctuate due to the partial or complete plugging of the first channel by the fluid emerging from the second channel. To measure the pressure fluctuations, a sensor such as a Laplace sensor may be positioned in the first channel upstream of the intersection, e.g., as shown in FIG. 13 with first channel 800, second channel 810, and sensor 815. Second channel 810 in this example is used to inject a fluid into first channel 800, in this case creating a new droplet 820 within channel 810. Early in the cycle, the emerging droplet at least partially plugs first channel 800, causing the pressure in the first channel to rise and interface 840 of sensor 815 to move upward, as shown in FIG. 13A. However, when the droplet 820 separates from the second channel, the pressure is released, causing interface 840 to move lower in sensor 815, as shown in FIG. 13B. Because the droplets produced via the second channel are produced in the first channel in a periodic cycle, the interface of the sensor oscillates up and down periodically. By tracking the position of the interface over many cycles, pressure fluctuations within the first channel may be determined or quantified during droplet formation. An example of such a determination can be seen in Example 4.

For example, early in the cycle, when the emerging droplet partially or completely plugs the first channel, there is a general ramping up of pressure within the first channel upstream of the intersection, as registered by the Laplace sensor. After plugging the orifice at the intersection of the first and second channels, the increased pressure impinges on the emerging droplet, causing the droplet to narrow and eventually pinch off to form an isolated droplet; this event may coincide with a rapid fall in pressure.

In various aspects of the invention, a fluidic system as disclosed herein may also include a droplet formation system, a sensing system, a controller, and/or a droplet sorting and/or separation system, or any combination of these systems. Such systems and methods may be positioned in any suitable order, depending on a particular application, and in some cases, multiple systems of a given type may be used, for example, two or more droplet formation systems, two or more droplet separation systems, etc. As examples of arrangements, systems of the invention can be arranged to form droplets, to dilute fluids, to control the concentration of species within droplets, to sort droplets to select those with a desired concentration of species or entities (e.g., droplets each containing one molecule of reactant), to fuse individual droplets to cause reaction between species contained in the individual droplets, to determine reaction(s) and/or rates of reaction(s) in one or more droplets, etc. Many other arrangements can be practiced in accordance with the invention.

One aspect of the invention relates to systems and methods for producing droplets of fluid surrounded by a liquid. The fluid and the liquid may be substantially immiscible in many cases, i.e., immiscible on a time scale of interest (e.g., the time it takes a fluidic droplet to be transported through a particular system or device). In certain cases, the droplets may each be substantially the same shape or size, as further described below. The fluid may also contain other species, for example, certain molecular species (e.g., as further discussed below), cells, particles, etc.

In one set of embodiments, electric charge may be created on a fluid surrounded by a liquid, which may cause the fluid to separate into individual droplets within the liquid. In some embodiments, the fluid and the liquid may be present in a channel, e.g., a microfluidic channel, or other constricted space that facilitates application of an electric field to the fluid (which may be "AC" or alternating current, "DC" or direct current etc.), for example, by limiting movement of the fluid with respect to the liquid. Thus, the fluid can be present as a series of individual charged and/or electrically inducible droplets within the liquid. In one embodiment, the electric force exerted on the fluidic droplet may be large enough to cause the droplet to move within the liquid. In some cases, the electric force exerted on the fluidic droplet may be used to direct a desired motion of the droplet within the liquid, for example, to or within a channel or a microfluidic channel (e.g., as further described herein), etc.

Electric charge may be created in the fluid within the liquid using any suitable technique, for example, by placing the fluid within an electric field (which may be AC, DC, etc.), and/or causing a reaction to occur that causes the fluid to have an electric charge, for example, a chemical reaction, an ionic reaction, a photocatalyzed reaction, etc. In one embodiment, the fluid is an electrical conductor. As used herein, a "conductor" is a material having a conductivity of at least about the conductivity of 18 megaohm (MOhm or MΩ) water. The liquid surrounding the fluid may have a conductivity less than that of the fluid. For instance, the liquid may be an insulator, relative to the fluid, or at least a "leaky insulator," i.e., the liquid is able to at least partially electrically insulate the fluid for at least a short period of time. Those of ordinary skill in the art will be able to identify the conductivity of fluids. In one non-limiting embodiment, the fluid may be substantially hydrophilic, and the liquid surrounding the fluid may be substantially hydrophobic.

The electric field, in some embodiments, is generated from an electric field generator, i.e., a device or system able to create an electric field that can be applied to the fluid. The electric field generator may produce an AC field (i.e., one that varies periodically with respect to time, for example, sinusoidally, sawtooth, square, etc.), a DC field (i.e., one that is constant with respect to time), a pulsed field, etc. The electric field generator may be constructed and arranged to create an electric field within a fluid contained within a channel or a microfluidic channel. The electric field generator may be integral to or separate from the fluidic system containing the channel or microfluidic channel, according to some embodiments.

Techniques for producing a suitable electric field (which may be AC, DC, etc.) are known to those of ordinary skill in the art. For example, in one embodiment, an electric field is produced by applying voltage across a pair of electrodes, which may be positioned on or embedded within the fluidic system (for example, within a substrate defining the channel or microfluidic channel), and/or positioned proximate the fluid such that at least a portion of the electric field interacts with the fluid. The electrodes can be fashioned from any suitable electrode material or materials known to those of ordinary skill in the art, including, but not limited to, silver, gold, copper, carbon, platinum, copper, tungsten, tin, cadmium, nickel, indium tin oxide ("ITO"), etc., as well as combinations thereof. In some cases, transparent or substantially transparent electrodes can be used. In certain embodiments, the electric field generator can be constructed and arranged (e.g., positioned) to create an electric field applicable to the fluid of at least about 0.01 V/micrometer, and, in some cases, at least about 0.03 V/micrometer, at least about 0.05 V/micrometer, at least about 0.08 V/micrometer, at least about 0.1 V/micrometer, at least about 0.3 V/micrometer, at least about 0.5 V/micrometer, at least about 0.7 V/micrometer, at least about 1 V/micrometer, at least about 1.2 V/micrometer, at least about 1.4 V/micrometer, at least about 1.6 V/micrometer, or at least about 2 V/micrometer. In some embodiments, even higher electric field intensities may be used, for example, at least about 2 V/micrometer, at least about 3 V/micrometer, at least about 5 V/micrometer, at least about 7 V/micrometer, or at least about 10 V/micrometer or more.

In another aspect, the invention relates to systems and methods for allowing the mixing of more than one fluid to occur. For example, in various embodiments of the invention, two or more fluidic droplets may be allowed to fuse or coalesce, as described above, and then, within the fused droplet, the two or more fluids from the two or more original fluidic droplets may then be allowed to mix. It should be noted that when two droplets fuse or coalesce, perfect mixing within the droplet does not instantaneously occur. Instead, for example, the coalesced droplet may initially be formed of a first fluid region and a second fluid region. In some cases, the fluid regions may remain as separate regions, for example, due to internal "counter-revolutionary" flow within the fluidic droplet, thus resulting in a non-uniform fluidic droplet However, in other cases, the fluid regions within the fluidic droplet may be allowed to mix, react, or otherwise interact with each other, resulting in mixed or partially mixed fluidic droplets. The mixing may occur through natural means, for example, through diffusion (e.g., through the interface between the regions), through reaction of the fluids with each other, through fluid flow within the droplet (i.e., convection), etc. However, in some cases, mixing of the regions may be enhanced through certain systems external of the fluidic droplet. For example, the fluidic droplet may be passed through one or more channels or other systems which cause the droplet to change its velocity and/or direction of movement. The change of direction may alter convection patterns within the droplet, causing the fluids to be at least partially mixed.

Other examples of fluidic mixing in droplets are described in International Patent Application Serial No. PCT/US2004/010903, filed Apr. 9, 2004 by Link, et al., incorporated herein by reference.

In another set of embodiments, droplets of fluid can be created from a fluid surrounded by a liquid within a channel by altering the channel dimensions in a manner that is able to induce the fluid to form individual droplets, for example, using flow-focusing techniques. The channel may, for example, be a channel that expands relative to the direction of flow, e.g., such that the fluid does not adhere to the channel walls and forms individual droplets instead, or a channel that narrows relative to the direction of flow, e.g., such that the fluid is forced to coalesce into individual droplets. In other embodiments, internal obstructions may also be used to cause droplet formation to occur. For instance, baffles, ridges, posts, or the like may be used to disrupt liquid flow in a manner that causes the fluid to coalesce into fluidic droplets.

Other examples of the production of droplets of fluid surrounded by a liquid are described in International Patent Application Serial No. PCT/US2004/010903, filed Apr. 9, 2004 by Link, et al. and International Patent Application Ser. No. PCT/US03/20542, filed Jun. 30, 2003 by Stone, et al., published as WO 2004/002627 on Jan. 8, 2004, each incorporated herein by reference.

In some embodiments, the fluidic droplets may each be substantially the same shape and/or size. The shape and/or size can be determined, for example, by measuring the average diameter or other characteristic dimension of the droplets. The term "determining," as used herein, generally refers to the analysis or measurement of a species, for example, quantitatively or qualitatively, and/or the detection of the presence or absence of the species. "Determining" may also refer to the analysis or measurement of an interaction between two or more species, for example, quantitatively or qualitatively, or by detecting the presence or absence of the interaction. Examples of suitable techniques include, but are not limited to, spectroscopy such as infrared, absorption, fluorescence, UV/visible, FTIR ("Fourier Transform Infrared Spectroscopy"), or Raman; gravimetric techniques; ellipsometry; piezoelectric measurements; immunoassays; electrochemical measurements; optical measurements such as optical density measurements; circular dichroism; light scattering measurements such as quasi-electric light scattering; polarimetry; refractometry; or turbidity measurements.

The "average diameter" of a plurality or series of droplets is the arithmetic average of the average diameters of each of the droplets. Those of ordinary skill in the art will be able to determine the average diameter (or other characteristic dimension) of a plurality or series of droplets, for example, using laser light scattering, microscopic examination, or other known techniques. The diameter of a droplet, in a non-spherical droplet, is the mathematically-defined average diameter of the droplet, integrated across the entire surface. The average diameter of a droplet (and/or of a plurality or series of droplets) may be, for example, less than about 1 mm, less than about 500 micrometers, less than about 200 micrometers, less than about 100 micrometers, less than about 75 micrometers, less than about 50 micrometers, less than about 25 micrometers, less than about 10 micrometers, or less than about 5 micrometers in some cases. The average diameter may also be at least about 1 micrometer, at least about 2 micrometers, at least about 3 micrometers, at least about 5 micrometers, at least about 10 micrometers, at least about 15 micrometers, or at least about 20 micrometers in certain cases.

In certain embodiments of the invention, the fluidic droplets may contain additional entities, for example, other chemical, biochemical, or biological entities (e.g., dissolved or suspended in the fluid), cells, particles, gases, molecules, or the like. In some cases, the droplets may each be substantially the same shape or size, as discussed above. In certain instances, the invention provides for the production of droplets consisting essentially of a substantially uniform number of entities of a species therein (i.e., molecules, cells, particles, etc.). For example, about 90%, about 93%, about 95%, about 97%, about 98%, or about 99%, or more of a plurality or series of droplets may each contain the same number of entities of a particular species. For instance, a substantial number of fluidic droplets produced, e.g., as described above, may each contain 1 entity, 2 entities, 3 entities, 4 entities, 5 entities, 7 entities, 10 entities, 15 entities, 20 entities, 25 entities, 30 entities, 40 entities, 50 entities, 60 entities, 70 entities, 80 entities, 90 entities, 100 entities, etc., where the entities are molecules or macromolecules, cells, particles, etc. In some cases, the droplets may each independently contain a range of entities, for example, less than 20 entities, less than 15 entities, less than 10 entities, less than 7 entities, less than 5 entities, or less than 3 entities in some cases. In one set of embodiments, in a liquid containing droplets of fluid, some of which contain a species of interest and some of which do not contain the species of interest, the droplets of fluid may be screened or sorted for those droplets of fluid containing the species as further described below (e.g., using fluorescence or other techniques such as those described above), and in some cases, the droplets may be screened or sorted for those droplets of fluid containing a particular number or range of entities of the species of interest, e.g., as previously described.

In another aspect, the invention relates to systems and methods for splitting a fluidic droplet into two or more droplets. The fluidic droplet may be surrounded by a liquid, e.g., as previously described, and the fluid and the liquid are essentially immiscible in some cases. The two or more droplets created by splitting the original fluidic droplet may each be substantially the same shape and/or size, or the two or more droplets may have different shapes and/or sizes, depending on the conditions used to split the original fluidic droplet.

According to one set of embodiments, a fluidic droplet can be split using an applied electric field. The electric field may be an AC field, a DC field, etc. The fluidic droplet, in this embodiment, may have a greater electrical conductivity than the surrounding liquid, and, in some cases, the fluidic droplet may be neutrally charged. In some embodiments, the droplets produced from the original fluidic droplet are of approximately equal shape and/or size. In certain embodiments, in an applied electric field, electric charge may be urged to migrate from the interior of the fluidic droplet to the surface to be distributed thereon, which may thereby cancel the electric field experienced in the interior of the droplet. In some embodiments, the electric charge on the surface of the fluidic droplet may also experience a force due to the applied electric field, which causes charges having opposite polarities to migrate in opposite directions. The charge migration may, in some cases, cause the drop to be pulled apart into two separate fluidic droplets. The electric field applied to the fluidic droplets may be created, for example, using the techniques described above, such as with a reaction an electric field generator, etc.

Other examples of splitting a fluidic droplet into two droplets are described in International Patent Application Serial No. PCT/US2004/010903, filed Apr. 9, 2004 by Link, et al.; U.S. Provisional Patent Application Ser. No. 60/498, 091, filed Aug. 27, 2003, by Link, et. al.; and International Patent Application Serial No. PCT/US03/20542, filed Jun. 30, 2003 by Stone, et al., published as WO 2004/002627 on Jan. 8, 2004, each incorporated herein by reference.

In one set of embodiments, a fluidic droplet may be directed by creating an electric charge (e.g., as previously described) on the droplet, and steering the droplet using an applied electric field, which may be an AC field, a DC field, etc. As an example, an electric field may be selectively applied and removed (or a different electric field may be applied) as needed to direct the fluidic droplet to a particular region. The electric field may be selectively applied and removed as needed, in some embodiments, without substantially altering the flow of the liquid containing the fluidic droplet.

In other embodiments, however, the fluidic droplets may be screened or sorted within a fluidic system of the invention by altering the flow of the liquid containing the droplets. For instance, in one set of embodiments, a fluidic droplet may be steered or sorted by directing the liquid surrounding the fluidic droplet into a first channel, a second channel, etc.

In certain aspects of the invention, sensors are provided that can sense and/or determine one or more characteristics of the fluidic droplets, and/or a characteristic of a portion of the fluidic system containing the fluidic droplet (e.g., the liquid surrounding the fluidic droplet) in such a manner as to allow the determination of one or more characteristics of the fluidic droplets. Characteristics determinable with respect to the droplet and usable in the invention can be identified by those of ordinary skill in the art. Non-limiting examples of such characteristics include fluorescence, spectroscopy (e.g., optical, infrared, ultraviolet, etc.), radioactivity, mass, volume, density, temperature, viscosity, pH, concentration of a substance, such as a biological substance (e.g., a protein, a nucleic acid, etc.), or the like.

A variety of definitions are now provided which will aid in understanding various aspects of the invention. Following, and interspersed with these definitions, is further disclosure that will more fully describe the invention.

As noted, various aspects of the present invention relate to droplets of fluid surrounded by a liquid (e.g., suspended). The droplets may be of substantially the same shape and/or size, or of different shapes and/or sizes, depending on the particular application. As used herein, the term "fluid" generally refers to a substance that tends to flow and to conform to the outline of its container, i.e., a liquid, a gas, a viscoelastic fluid, etc. Typically, fluids are materials that are unable to withstand a static shear stress, and when a shear stress is applied, the fluid experiences a continuing and permanent distortion. The fluid may have any suitable viscosity that permits flow. If two or more fluids are present, each fluid may be independently selected among essentially any fluids (liquids, gases, and the like) by those of ordinary skill in the art, by considering the relationship between the fluids. The fluids may each be miscible or immiscible. For example, two fluids can be selected to be essentially immiscible within the time frame of formation of a stream of fluids, or within the time frame of reaction or interaction. Where the portions remain liquid for a significant period of time, then the fluids should be essentially immiscible. Where, after contact and/or formation, the dispersed portions are quickly hardened by polymerization or the like, the fluids need not be as immiscible. Those of ordinary skill in the art can select suitable miscible or immiscible fluids, using contact angle measurements or the like, to carry out the techniques of the invention.

As used herein, a first entity is "surrounded" by a second entity if a closed planar loop can be drawn around the first entity through only the second entity. A first entity is "completely surrounded" if closed loops going through only the second entity can be drawn around the first entity regardless of direction (orientation of the loop). In one embodiment, the first entity is a cell, for example, a cell suspended in media is surrounded by the media. In another embodiment, the first entity is a particle. In yet another embodiment, the first entity is a fluid. The second entity may also be a fluid in some cases (e.g., as in a suspension, an emulsion, etc.), for example, a hydrophilic liquid may be suspended in a hydrophobic liquid, a hydrophobic liquid may be suspended in a hydrophilic liquid, a gas bubble may be suspended in a liquid, etc. Typically, a hydrophobic liquid and a hydrophilic liquid are essentially immiscible with respect to each other, where the hydrophilic liquid has a greater affinity to water than does the hydrophobic liquid. Examples of hydrophilic liquids include, but are not limited to, water and other aqueous solutions comprising water, such as cell or biological media, salt solutions, etc., as well as other hydrophilic liquids such as ethanol. Examples of hydrophobic liquids include, but are not limited to, oils such as hydrocarbons, silicone oils, mineral oils, fluorocarbon oils, organic solvents etc. Other examples of suitable fluids have been previously described.

Similarly, a "droplet," as used herein, is an isolated portion of a first fluid that is completely surrounded by a second fluid. It is to be noted that a droplet is not necessarily spherical, but may assume other shapes as well, for example, depending on the external environment. In one embodiment, the droplet has a minimum cross-sectional dimension that is substantially equal to the largest dimension of the channel perpendicular to fluid flow in which the droplet is located.

As mentioned, in some, but not all embodiments, the systems and methods described herein may include one or more microfluidic components, for example, one or more microfluidic channels. "Microfluidic," as used herein, refers to a device, apparatus or system including at least one fluid channel having a cross-sectional dimension of less than 1 mm, and a ratio of length to largest cross-sectional dimension of at least 3:1. A "microfluidic channel," as used herein, is a channel meeting these criteria. The "cross-sectional dimension" of the channel is measured perpendicular to the direction of fluid flow within the channel. Thus, some or all of the fluid channels in microfluidic embodiments of the invention may have maximum cross-sectional dimensions less than 2 mm, and in certain cases, less than 1 mm. In one set of embodiments, all fluid channels containing embodiments of the invention are microfluidic or have a largest cross sectional dimension of no more than 2 mm or 1 mm. In certain embodiments, the fluid channels may be formed in part by a single component (e.g. an etched substrate or molded unit). Of course, larger channels, tubes, chambers, reservoirs, etc. can be used to store fluids and/or deliver fluids to various components or systems of the invention. In one set of embodiments, the maximum cross-sectional dimension of the channel(s) containing embodiments of the invention is less than 500 microns, less than 200 microns, less than 100 microns, less than 50 microns, or less than 25 microns.

A "channel," as used herein, means a feature on or in an article (substrate) that at least partially directs flow of a fluid. The channel can have any cross-sectional shape (circular, oval, triangular, irregular, square or rectangular, or the like) and can be covered or uncovered. In embodiments where it is completely covered, at least one portion of the channel can have a cross-section that is completely enclosed, or the entire channel may be completely enclosed along its entire length with the exception of its inlet(s) and/or outlet(s). A channel may also have an aspect ratio (length to average cross sectional dimension) of at least 2:1, more typically at least 3:1, 5:1, 10:1, 15:1, 20:1, or more. An open channel generally will include characteristics that facilitate control over fluid transport, e.g., structural characteristics (an elongated indentation) and/or physical or chemical characteristics (hydrophobicity vs. hydrophilicity) or other characteristics that can exert a force (e.g., a containing force) on a fluid. The fluid within the channel may partially or completely fill the channel. In some cases where an open channel is used, the fluid may be held within the channel, for example, using surface tension (i.e., a concave or convex meniscus).

The channel may be of any size, for example, having a largest dimension perpendicular to fluid flow of less than about 5 mm or 2 mm, or less than about 1 mm, or less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 nm, or less than about 10 nm. In some cases the dimensions of the channel may be chosen such that fluid is able to freely flow through the article or substrate. The dimensions of the channel may also be chosen, for example, to allow a certain volumetric or linear flowrate of fluid in the channel. Of course, the number of channels and the shape of the channels can be varied by any method known to those of ordinary skill in the art. In some cases, more than one channel or capillary may be used. For example, two or more channels may be used, where they are positioned inside each other, positioned adjacent to each other, positioned to intersect with each other, etc.

In one set of embodiments, the fluidic droplets may contain cells or other entities, such as proteins, viruses, macromolecules, particles, etc. As used herein, a "cell" is given its ordinary meaning as used in biology. The cell may be any cell or cell type. For example, the cell may be a bacterium or other single-cell organism, a plant cell, or an animal cell.

A variety of materials and methods, according to certain aspects of the invention, can be used to form any of the above-described components of the systems and devices of the invention. In some cases, the various materials selected lend themselves to various methods. For example, various components of the invention can be formed from solid materials, in which the channels can be formed via micromachining, film deposition processes such as spin coating and chemical vapor deposition, laser fabrication, photolithographic techniques, etching methods including wet chemical or plasma processes, and the like. See, for example, *Scientific American,* 248:44-55, 1983 (Angell, et al). In one embodiment, at least a portion of the fluidic system is formed of silicon by etching features in a silicon chip. In some cases, one or more microfluidic channels may be defined in a solid material, and in some cases, various microfluidic channels may be defined in separate solid or planar materials that are physically contacted together. For instance, a first planar material may contain a first fluidic channel, and a second planar material may contain a second fluidic channel, where the materials are physically contacted together and an orifice defined between the first and second planar materials such that fluid can flow from the second channel into the first channel, e.g., through an orifice, using the systems and methods discussed above. Technologies for precise and efficient fabrication of various fluidic systems and devices of the invention from silicon are known. In another embodiment, various components of the systems and devices of the invention can be formed of a polymer, for example, an elastomeric polymer such as polydimethylsiloxane ("PDMS"), polytetrafluoroethylene ("PTFE" or Teflon®), or the like.

Different components can be fabricated of different materials. For example, a base portion including a bottom wall and side walls can be fabricated from an opaque material such as silicon or PDMS, and a top portion can be fabricated from a transparent or at least partially transparent material, such as glass or a transparent polymer, for observation and/or control of the fluidic process. Components can be coated so as to expose a desired chemical functionality to fluids that contact interior channel walls, where the base supporting material does not have a precise, desired functionality. For example, components can be fabricated as illustrated, with interior channel walls coated with another material. Material used to fabricate various components of the systems and devices of the invention, e.g., materials used to coat interior walls of fluid channels, may desirably be selected from among those materials that will not adversely affect or be affected by fluid flowing through the fluidic system, e.g., material(s) that is chemically inert in the presence of fluids to be used within the device.

In one embodiment, various components of the invention are fabricated from polymeric and/or flexible and/or elastomeric materials, and can be conveniently formed of a hardenable fluid, facilitating fabrication via molding (e.g. replica molding, injection molding, cast molding, etc.). The hardenable fluid can be essentially any fluid that can be induced to solidify, or that spontaneously solidifies, into a solid capable of containing and/or transporting fluids contemplated for use in and with the fluidic network. In one embodiment, the hardenable fluid comprises a polymeric liquid or a liquid polymeric precursor (i.e. a "prepolymer"). Suitable polymeric liquids can include, for example, thermoplastic polymers, thermoset polymers, or mixture of such polymers heated above their melting point. As another example, a suitable polymeric liquid may include a solution of one or more polymers in a suitable solvent, which solution forms a solid polymeric material upon removal of the solvent, for example, by evaporation. Such polymeric materials, which can be solidified from, for example, a melt state or by solvent evaporation, are well known to those of ordinary skill in the art. A variety of polymeric materials, many of which are elastomeric, are suitable, and are also suitable for forming molds or mold masters, for embodiments where one or both of the mold masters is composed of an elastomeric material. A non-limiting list of examples of such polymers includes polymers of the general classes of silicone polymers, epoxy polymers, and acrylate polymers. Epoxy polymers are characterized by the presence of a three-membered cyclic ether group commonly referred to as an epoxy group, 1,2-epoxide, or oxirane. For example, diglycidyl ethers of bisphenol A can be used, in addition to compounds based on aromatic amine, triazine, and cycloaliphatic backbones. Another example includes the well-known Novolac polymers. Non-limiting examples of silicone elastomers suitable for use according to the invention include those formed from precursors including the chlorosilanes such as methylchlorosilanes, ethylchlorosilanes, phenylchlorosilanes, etc.

Silicone polymers are preferred in one set of embodiments, for example, the silicone elastomer polydimethylsiloxane. Non-limiting examples of PDMS polymers include those sold under the trademark Sylgard by Dow Chemical Co., Midland, Mich., and particularly Sylgard 182, Sylgard 184, and Sylgard 186. Silicone polymers including PDMS have several beneficial properties simplifying fabrication of the microfluidic structures of the invention. For instance, such materials are inexpensive, readily available, and can be solidified from a prepolymeric liquid via curing with heat. For example, PDMSs are typically curable by exposure of the prepolymeric liquid to temperatures of about, for example, about 65° C. to about 75° C. for exposure times of, for example, about an hour. Also, silicone polymers, such as PDMS, can be elastomeric and thus may be useful for forming very small features with relatively high aspect ratios, necessary in certain embodiments of the invention. Flexible (e.g., elastomeric) molds or masters can be advantageous in this regard.

One advantage of forming structures such as microfluidic structures of the invention from silicone polymers, such as PDMS, is the ability of such polymers to be oxidized, for example by exposure to an oxygen-containing plasma such as an air plasma, so that the oxidized structures contain, at their surface, chemical groups capable of cross-linking to other oxidized silicone polymer surfaces or to the oxidized surfaces of a variety of other polymeric and non-polymeric materials. Thus, components can be fabricated and then oxidized and essentially irreversibly sealed to other silicone polymer surfaces, or to the surfaces of other substrates reactive with the oxidized silicone polymer surfaces, without the need for separate adhesives or other sealing means. In most cases, sealing can be completed simply by contacting an oxidized silicone surface to another surface without the need to apply auxiliary pressure to form the seal. That is, the pre-oxidized silicone surface acts as a contact adhesive against suitable mating surfaces. Specifically, in addition to being irreversibly sealable to itself, oxidized silicone such as oxidized PDMS can also be sealed irreversibly to a range of oxidized materials other than itself including, for example, glass, silicon, silicon oxide, quartz, silicon nitride, polyethylene, polystyrene, glassy carbon, and epoxy polymers, which have been oxidized in a similar fashion to the PDMS surface (for example, via exposure to an oxygen-containing plasma). Oxidation and sealing methods useful in the context of the present invention, as well as overall molding techniques, are described in the art, for example, in an article entitled "Rapid Prototyping of Microfluidic Systems and Polydimethylsiloxane," *Anal. Chem.*, 70:474-480, 1998 (Duffy et al.), incorporated herein by reference.

Another advantage to forming microfluidic structures of the invention (or interior, fluid-contacting surfaces) from oxidized silicone polymers is that these surfaces can be much more hydrophilic than the surfaces of typical elastomeric polymers (where a hydrophilic interior surface is desired). Such hydrophilic channel surfaces can thus be more easily filled and wetted with aqueous solutions than can structures comprised of typical, unoxidized elastomeric polymers or other hydrophobic materials.

In one embodiment, a bottom wall is formed of a material different from one or more side walls or a top wall, or other components. For example, the interior surface of a bottom wall can comprise the surface of a silicon wafer or microchip, or other substrate. Other components can, as described above, be sealed to such alternative substrates. Where it is desired to seal a component comprising a silicone polymer (e.g. PDMS) to a substrate (bottom wall) of different material, the substrate may be selected from the group of materials to which oxidized silicone polymer is able to irreversibly seal (e.g., glass, silicon, silicon oxide, quartz, silicon nitride, polyethylene, polystyrene, epoxy polymers, and glassy carbon surfaces which have been oxidized). Alternatively, other sealing techniques can be used, as would be apparent to those of ordinary skill in the art, including, but not limited to, the use of separate adhesives, thermal bonding, solvent bonding, ultrasonic welding, etc.

Combinations of these and/or other systems and methods of controlling and manipulating of fluids are also envisioned, for example, systems and methods as disclosed in U.S. patent application Ser. No. 11/360,845, filed Feb. 23, 2006, by Link, et. al.; U.S. Pat. No. 5,512,131, issued Apr. 30, 1996 to Kumar, et al.; International Patent Publication WO 96/29629, published Jun. 26, 1996 by Whitesides, et al.; U.S. Pat. No. 6,355,198, issued Mar. 12, 2002 to Kim, et al.; International Patent Application Serial No.: PCT/US01/16973, filed May 25, 2001 by Anderson, et al., published as WO 01/89787 on Nov. 29, 2001; International Patent Application Serial No. PCT/US03/20542, filed Jun. 30, 2003 by Stone, et al., published as WO 2004/002627 on Jan. 8, 2004; International Patent Application Serial No. PCT/US2004/010903, filed Apr. 9, 2004 by Link, et al.; U.S. patent application Ser. No. 11/246,911, filed Oct. 7, 2005, by Link, et al.; and U.S. patent application Ser. No. 61/098,674, filed Sep. 19, 2008 by Weitz et al., each of which is incorporated herein by reference.

The following examples are intended to illustrate certain embodiments of the present invention, but do not exemplify the full scope of the invention.

Example 1

Figure 6:
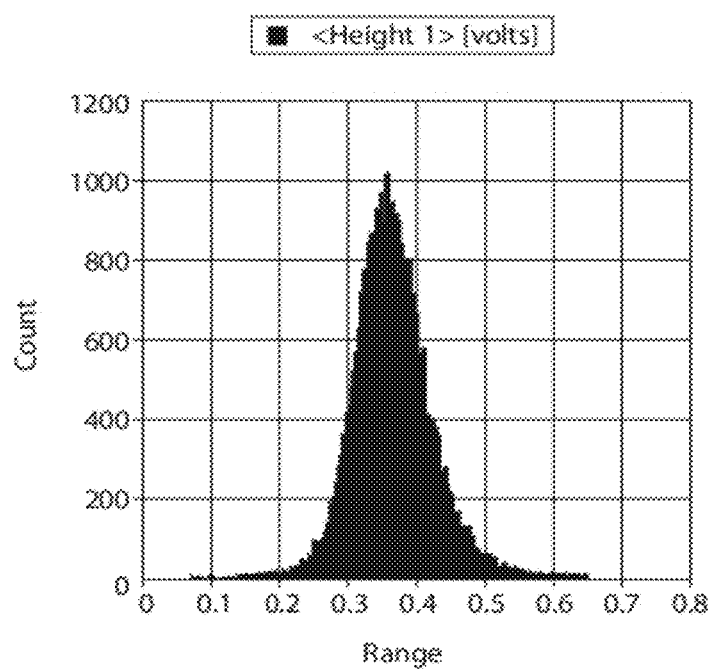
FIG. 6 shows a plot of droplet size distribution in accordance with an embodiment of the invention.

This example demonstrates fluid injection into fluidic droplets. In each of Examples 1, 2, and 3, single-layer PDMS microfluidic devices such as those shown in FIGS. 4A and 4B were fabricated. In these examples, water-in-oil emulsion droplets with relatively low polydispersity flowed past the orifice where an electric field was applied to cause injection of a bromophenol dyed fluid into the droplets. The droplets passed through a serpentine channel (e.g., as shown in FIGS. 4A and 4B) where the bromophenol dye mixed with the fluid inside the droplets. The droplets then flowed past a laser beam/PMT (photomultiplier tube) setup and microscope camera, both of which captured the light intensity inside the droplets. Since the volume of each droplet prior to injection is known and essentially the same, the amount of bromophenol dyed fluid injected could be determined from the change in intensity of the droplet after injection. Measurements from the PMT/laser were compared to images captured by the camera to ensure consistency. Approximately 1,000 droplets were sampled for each data point. An example of such an experiment is shown in FIG. 6. In this figure, the number size distribution indicates that fluid was injected into the droplets with a relatively narrow distribution.

Example 2

Figure 7A:
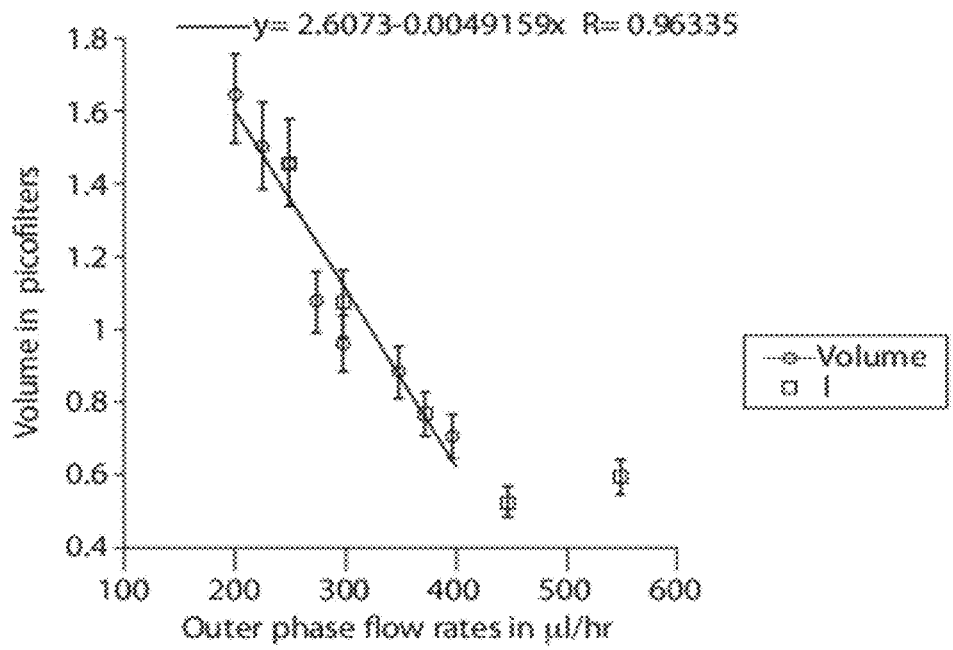
FIGS. 7A-7B show plots of control of injection volume in other embodiments of the invention.

This example demonstrates control of fluid injection by varying the continuous phase (i.e., the "outer phase") flow rate. A system similar to that discussed in Example 1 was used for this example. The outer phase flow rate was set by a volume-driven syringe pump and was varied while keeping the other operating conditions (i.e., applied voltage) constant. As shown in FIG. 7A, as the outer phase flow rate increased, the residence time of droplets decreased, resulting in a decrease in the volume of fluid injected. Thus, by controlling the outer phase flow rate, the amount of fluid injected into the droplets could be readily controlled.

Example 3

Figure 7B:
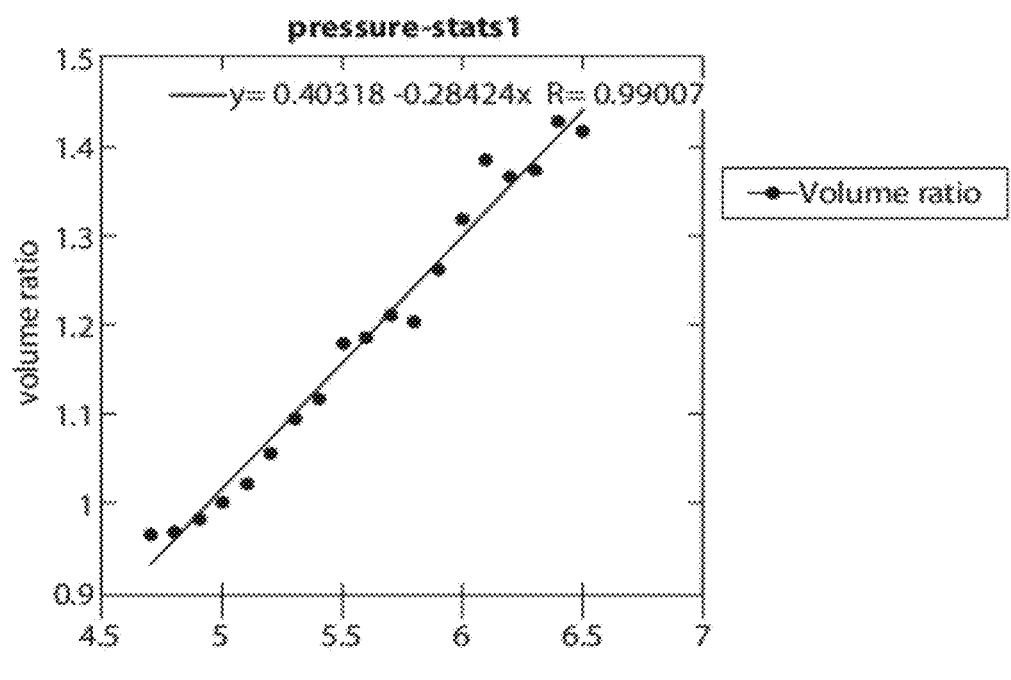

This example demonstrates control of fluid injection by varying the injection pressure. A system similar to that discussed in Example 1 was used for this example. The fluid tubing leading into the second channel containing a bromophenol dye was placed in a pressure tight basin fed by regulator-controlled pressurized air. As the injection pressure increased, the injection volume increased, as shown in FIG. 7B (pressure in units of ps). Accordingly, by controlling the injection pressure, the amount of fluid injected into the droplets could be readily controlled.

Example 4

This example illustrates the determination of pressure in a fluidic channel locally and with high temporal resolution, in another embodiment of the invention.

FIG. 12 illustrates the Laplace sensors used in this example to measure channel pressure locally and with high temporal resolution. In FIG. 12A, first channel 850 and second channel 860 meet at intersection 870. However, prior to intersection 870, first channel 850 and second channel 860 run substantially parallel to each other. Second channel ends at orifice 865 at intersection 870. First channel 850 contains a first, outer fluid while second channel 860 contains a second, inner fluid (in these figures, the fluids appear as different colors, and the terms "inner" and "outer" are used for purposes of clarity only). The fluidic interface between these fluids is balanced at the orifice by adjusting the pressures of the two fluids. By controlling the pressures within the first and second channels, as is shown in FIG. 12B, the interface between the two fluids may be controlled to adopt a shape with fixed curvature such that the pressure jump across the interface is equal to the pressure differential inside and outside. In FIG. 12C, by measuring the distance of the interface below the plane of the orifice, the radius of curvature of the bulge can be calculated. Using Laplace's Law, this can then be used to calculate the pressure in a channel, e.g., using an optical measurement of the location of the interface.

The following is an explanation of how the location of the interface can be used to calculate the pressure in a channel. However, it should be understood that this discussion is not meant to be limiting. When the interface between the two fluids is balanced in the orifice, the pressure differential between the inner (second) and outer (first) fluids is equal to the Laplace pressure jump across the interface, $$P_{out} - P_{in} = \gamma/r.$$

For fixed $P_{in}$, the radius of curvature of the interface r depends on $P_{out}$: if $P_{out}$ is small, the interface is positioned relatively low in the orifice, adopting a shape of high curvature, whereas if it is large, it is positioned relatively high in the orifice, adopting a flatter shape with lower curvature. If the pressure fluctuates in time, the interface may move to maintain mechanical equilibrium in each instant. Thus, the value of r(t) can be used to indirectly calculate $P_{out}(t)$ at each time point. To obtain r(t), h(t) can be determined, where h(t) is the distance of the lowest part of the interface from the plane of the orifice, as shown in FIG. 12. For example, for a circular orifice, $$r(t) = \frac{1}{2}[h(t) + d^2/h(t)].$$

Since $P_{out}(t) = \gamma/r(t) + P_{in}$, this allows the pressure fluctuations to be determined by optically tracking the motion of the interface.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of" when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A microfluidic apparatus, comprising:
   a first microfluidic channel;
   a second microfluidic channel contacting the first microfluidic channel at an intersection defined by the first and second microfluidic channels, wherein the second microfluidic channel connects to the intersection via an orifice having a dimension of no more than about 90% of the average cross-sectional dimension of the second microfluidic channel, and wherein the orifice of the second microfluidic channel is sized to create a fluid interface between a fluid in the second microfluidic channel and a fluid in the first microfluidic channel having a radius of curvature that is smaller than the radius of curvature of a first droplet contained within the first microfluidic channel, the radius of curvature of the first droplet being defined in part by the cross-sectional dimension of the first microfluidic channel and the radius of curvature of a second droplet being defined in part by the cross-sectional dimension of the orifice of the second microfluidic channel;
   first and second electrodes positioned on opposing sides of the first microfluidic channel and the second microfluidic channel to create an electric field maximum within the intersection; and
   a controller configured to control voltage applied to the first and second electrodes to control fluid flow from the second microfluidic channel into the first microfluidic channel.

2. The apparatus of claim 1, wherein the first microfluidic channel, the second microfluidic channel, the first electrode, and the second electrode are positioned such that a plane intersects each of these.

3. The apparatus of claim 1, wherein the second microfluidic channel is substantially parallel the first microfluidic channel prior to the intersection.

4. The apparatus of claim 1, wherein the first microfluidic channel is substantially linear through the intersection with the second microfluidic channel.

5. The apparatus of claim 1, wherein the first microfluidic channel is defined in a first planar material, and the second microfluidic channel is defined in a second planar material.

6. The apparatus of claim 5, wherein the orifice is defined at a location where the first planar material and the second planar material physically contact each other.

7. The apparatus of claim 1, wherein the second microfluidic channel contacts the first microfluidic channel at a T-junction intersection.

8. The apparatus of claim 1, wherein the microfluidic apparatus further comprises a pressure source configured to vary pressure of a fluid within the second microfluidic channel.

9. The apparatus of claim 1, wherein the orifice has an average cross-sectional dimension less than about 30 microns.

10. The apparatus of claim 1, wherein the second microfluidic channel is tapered at the intersection with the first microfluidic channel.

11. The apparatus of claim 1, wherein the first microfluidic channel contains the first droplet.

12. A microfluidic apparatus, comprising:
    a first microfluidic channel;
    a second microfluidic channel contacting the first microfluidic channel at an intersection defined by the first and second microfluidic channels, wherein the second microfluidic channel connects to the intersection via an orifice having a dimension of no more than about 90% of the average cross-sectional dimension of the second microfluidic channel, and wherein the orifice of the second microfluidic channel is sized to create a fluid interface between a fluid in the second microfluidic channel and a fluid in the first microfluidic channel having a radius of curvature that is smaller than the radius of curvature of a first droplet contained within the first microfluidic channel, the radius of curvature of the first droplet being defined in part by the cross-sectional dimension of the first microfluidic channel and the radius of curvature of a second droplet being defined in part by the cross-sectional dimension of the orifice of the second microfluidic channel;
    first and second electrodes positioned on the same side of the first microfluidic channel to create an electric field maximum within the intersection; and a controller configured to control voltage applied to the first and second electrodes to control fluid flow from the second microfluidic channel into the first microfluidic channel.

13. The apparatus of claim 12, wherein the second microfluidic channel contacts the first microfluidic channel at a T-junction intersection.

14. The apparatus of claim 12, wherein the microfluidic apparatus further comprises a pressure source configured to vary pressure of a fluid within the second microfluidic channel.

15. The apparatus of claim 12, wherein the orifice has an average cross-sectional dimension less than about 30 microns.

16. The apparatus of claim 12, wherein the second microfluidic channel is tapered at the intersection with the first microfluidic channel.

17. The apparatus of claim 12, wherein the first microfluidic channel contains the first droplet.

18. A method, comprising:

providing a microfluidic apparatus comprising a first microfluidic channel and a second microfluidic channel contacting the first microfluidic channel at an intersection defined by the first and second microfluidic channels, wherein the second microfluidic channel connects to the intersection via an orifice having a dimension of no more than about 90% of the average cross-sectional dimension of the second microfluidic channel, and wherein the orifice of the second microfluidic channel is sized to create a fluid interface between a fluid in the second microfluidic channel and a fluid in the first microfluidic channel having a radius of curvature that is smaller than the radius of curvature of a first droplet contained within the first microfluidic channel, the radius of curvature of the first droplet being defined in part by the cross-sectional dimension of the first microfluidic channel and the radius of curvature of a second droplet being defined in part by the cross-sectional dimension of the orifice of the second microfluidic channel;

flowing a droplet through the first microfluidic channel towards an electric field maximum within the intersection, the electric field maximum created by first and second electrodes positioned on opposing sides of the first microfluidic channel and the second microfluidic channel; and controlling flow of fluid from the second microfluidic channel into the droplet using a controller configured to control voltage applied to the first and second electrodes.

* * * * *